US008110356B2

(12) United States Patent
Nicolaides et al.

(10) Patent No.: US 8,110,356 B2
(45) Date of Patent: *Feb. 7, 2012

(54) METHOD FOR GENERATING HYPERMUTABLE PLANTS

(75) Inventors: Nicholas C. Nicolaides, Boothwyn, PA (US); Luigi Grasso, Philadelphia, PA (US); Phillip M. Sass, Audubon, PA (US); Kenneth W. Kinzler, Bel Air, MD (US); Bert Vogelstein, Baltimore, MD (US)

(73) Assignees: The Johns Hopkins University, Baltimore, MD (US); Morphotek, Inc., Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/728,958

(22) Filed: Mar. 22, 2010

(65) Prior Publication Data

US 2011/0055964 A1   Mar. 3, 2011

Related U.S. Application Data

(60) Division of application No. 11/128,420, filed on May 13, 2005, now Pat. No. 7,704,689, which is a continuation of application No. 09/749,601, filed on Dec. 28, 2000, now Pat. No. 6,900,370.

(60) Provisional application No. 60/183,333, filed on Feb. 18, 2000.

(51) Int. Cl.
*C12Q 1/68* (2006.01)
*C12N 15/82* (2006.01)

(52) U.S. Cl. .................................... 435/6.1; 800/288

(58) Field of Classification Search ........................ None
See application file for complete search history.

(56) References Cited

U.S. PATENT DOCUMENTS

| 5,907,079 | A | 5/1999 | Mak et al. |
| 6,146,894 | A | 11/2000 | Nicolaides et al. |
| 6,191,268 | B1 | 2/2001 | Liskay et al. |
| 6,287,862 | B1 | 9/2001 | delCardayre et al. |

FOREIGN PATENT DOCUMENTS

| WO | WO 97 05268 A | | 2/1997 |
| WO | WO 97/08312 | | 3/1997 |
| WO | WO 99/19492 | * | 4/1999 |
| WO | WO 99 19492 A | | 4/1999 |

OTHER PUBLICATIONS

Allen, D., et al., "MutS mediates heteroduplex loop formation by a translocation mechanism" *EMBO J.*, 1997, 16(14), 4467-4476.
Baker, S.M., et al., "Male mice defective in the DNA mismatch repair gene PMS2 exhibit abnormal chromosome synapsis in meiosis" *Cell*, 1995, 82, 309-319.
Bronner C.E., et al., "Mutation in the DNA mismatch repair gene homologue hMLH1 is associated with hereditary non-polyposis colon cancer" *Nature*, 1994, 368, 258-261.
de Wind, N., et al., "Inactivation of the mouse Msh2 gene results in mismatch repair deficiency, methylation tolerance, hyperrecombination, and predisposition to cancer" *Cell*, 1995, 82, 321-330.
Drummond, J.T., et al., "Isolation of an hMSH2-p160 heterodimer that restores DNA mismatch repair to tumor cells" *Science*, 1995, 268, 1909-1912.
Drummond, J.T., et al., "Cisplatin and adriamycin resistance are associated with mutlα and mismatch repair deficiency in an ovarian tumor cell line" *J. Biological Chemistry*, 1996, 271(33), 19645-19648.
Edelmann, W., et al., "Meiotic pachytene arrest in MLH1-deficient mice" *Cell*, 1996, 85, 1125-1134.
Eshleman, J.R., et al., "Mismatch repair defects in human carcinogenesis" *Human Molecular Genetics*, 1996, 5, 1489-1494.
Fishel, R. et al. "The human mutator gene homolog MSH2 and its association with hereditary nonpolyposis colon cancer." *Cell* 1993, 7:1027-1038.
Galio, L., et al., "ATP hydrolysis-dependent formation of a dynamic ternary nucleoprotein complex with MutS and MutL" *Nucleic Acids Research*, 1999, 27(11), 2325-2331.
Hamilton, S.R. et al. "The molecular basis of Turcot's syndrome." *N. Eng. J. Med.* 1995, 332:839-847.
Harfe, B.D., "DNA mismatch repair and genetic instability" *Annu. Rev. Genet.*, 2000, 34, 359-399.
Hoang J., et al., "BAT-26, an Indicator of the Replication Error Phenotype in Colorectal Cancers and Cell Lines" *Cancer Res.*, 1997, 57, 300-303.
Holmes, J., S. Clark, and P. Modrich. "Strand-specific mismatch correction in nuclear extracts of human and *Drosophila melanogaster* cell lines" *Proc. Natl. Acad. Sci. USA* 1990 87:5837-5841.
Honma, M. et al., "Cytotoxic and Mutagenic Responses to X-rays and Chemical Mutagens in Normal and p53-mutated Human Lymphoblastoid Cells" *Mut. Res.*, 1997, 374, 89-98.
Jiricny, J., et al., "Mismatch repair defects in cancer" *Curr. Opin. Genet. Dev.*, 2000, 10, 157-161.
Karran, P., et al., "Genomic instability and tolerance to alkylating agents" *Cancer Surveys*, 1996, 28, 69-71.
Leach, F.S., et al., "Mutations of a mutS homolog in hereditary nonpolyposis colorectal cancer" *Cell*, 1993, 75, 1215-1225.
Li, G.-M. and P. Modrich. "Restoration of mismatch repair to nuclear extracts of H6 colorectal tumor cells by a heterodimer of human MutL homologs" *Proc. Natl. Acad. Sci. USA* 1995 92:1950-1954.

(Continued)

*Primary Examiner* — David H Kruse
(74) *Attorney, Agent, or Firm* — Banner and Witcoff, Ltd.

(57) ABSTRACT

Blockade of mismatch repair in a plant can lead to hypermutation and a new genotype and/or phenotype. One approach used to generate hypermutable plants is through the expression of dominant negative alleles of mismatch repair genes in transgenic plants or derived cells. By introducing these genes into cells and transgenic plants, new cell lines and plant varieties with novel and useful properties can be prepared more efficiently than by relying on the natural rate of mutation. Moreover, methods to inhibit the expression and activity of endogenous plant MMR genes and their encoded products are also useful to generate hypermutable plants.

12 Claims, 15 Drawing Sheets

OTHER PUBLICATIONS

Liu, T., et al., "Microsatellite instability as a predictor of a mutation in a DNA mismatch repair gene in familial colorectal cancer" *Genes, Chromosomes & Cancer*, 2000, 27, 17-25.

Liu et al., "Analysis of Mismatch Repair Genes in Hereditary Nonpolyposis Colorectal Cancer Patients" *Nature Medicine*, Feb. 1996, 2(2), 169-174.

Ma et al., "Dominant Negative Expression of hPMS2 Creates Isogenic Mismatch Repair Deficient Human Colon Cancer Cell Lines" *Proc. Am. Assoc. Cancer Res.*, Mar. 1998, 39, p. 460 (Abstract #3130).

McCallum, C.M., "Targeted screening for induced mutations" *Nature Biotechnology*, 2000, 18, 455-457.

Modrich, P., "Mismatch repair, genetic stability, and cancer" *Science*, 1994, 266, 1959-1960.

Nicolaides, N.C., et al., "The jun family members, c-jun and junD, transactivate the human c-*myb*, promotor via an Ap1-like element" *J. Biological Chemistry*, 1992, 267(27), 19655-19672.

Nicolaides, N.C., et al., "Genomic organization of the human *PMS2* gene family" *Genomics*, 1995, 30, 195-206.

Nicolaides, N.C. et al. "Molecular cloning of the N- terminus of GTBP." *Genomics* 1996, 31:395-397.

Nicolaides, N.C., et al., "Positive autoregulation of c-*myb*, expression via Myb binding sites in the 5' flanking region of the human c-*myb* gene" *Molecular and Cellular Biology*, 1991, 11(12), 6166-6176.

Nicolaides, N.C., "A naturally occurring *hPMS2* mutation can confer a dominant negative nutator phenotype" *Mol. Cell. Biol.*, 1998, 18(3), 1635-1641.

Nicolaides, N.C., et al., "Analysis of the 5' region of *PMS2* reveals heterogeneous transcripts and a novel overlapping gene" *Genomics*, 1995, 29, 329-334.

Nicolaides, N.C., et al., "Mutations of two PMS homologues in hereditary nonpolyposis colon cancer" *Nature*, 1994, 371, 75-80.

Palombo, F., et al., "Mismatch repair and cancer" *Nature*, 1994, 367, 417.

Pang, Q., T.A. Prolla and R.M. Liskay, "Functional domains of the *Saccharomyces cerevisiae* Mlh1p and Pms1p DNA mismatch repair proteins and their relevance to human hereditary nonpolyposis colorectal cancer-associated mutations" *Mol. Cell. Biol.* 1997 17(8):4465-4473.

Papadopoulos, N., et al., "Mutation of a *mutL* homolog in hereditary colon cancer" *Science*, 1994, 263, 1625-1629.

Papadopoulos, N., et al., "Mutations of *GTBP* in genetically unstable cells" *Science*, 1995, 268, 1915-1917.

Parsons, R. et al. "Mismatch repair deficiency in phenotypically normal human cells." *Science* 1995 268:738-740.

Parsons, R., et al., "hypermutability and mismatch repair deficiency in RER+ tumor cells" *Cell*, 1993, 75, 1227-1236.

Peinado, M.A., et al., "Isolation and characterization of allelic losses and gains in colorectal tumors by arbitrarily primed polymerase chain reaction" *Proc. Natl. Acad. Sci. USA*, 1992, 89, 10065-10069.

Perucho, M., et al., "Cancer of the microsatellite mutator phenotype" *Biol. Chem.*, 1996, 377, 675-684.

Prolla, T.A., et al., "MLH1, PMS1, and MSH2 interactions during the initiation of DNA mismatch repair in yeast" *Science*, 1994, 265, 1091-1093.

Quian, Y. et al., "Molecular events after antisense inhibition of hMSH2 in a HeLa cell line" *Mutation Research*, Oct. 12, 1998, vol. 418, pp. 61-71.

Spampinato, C., et al., "The MutL ATPase is required for mismatch repair" *J. Biological Chemistry*, 2000, 275(13), 9863-9869.

Strand, M., et al., "Destabilization of tracts of simple repetitive DNA in yeast by mutations affecting DNA mismatch repair" *Nature*, 1993, 365, 274-276.

Su, S., et al., "Mispair specificity of methyl-directed DNA mismatch correction in vitro" *J. Biological Chemistry*, 1988, 263(14), 6829-6835.

Vora, K.A. et al., "Severe Attenuation of the B Cell Immune Response in Msh2-deficient Mice" *Journal of Experimental Medicine*, Feb. 1999, 189(3), 471-481.

Wheeler, J.M.D., et al., "The role of hypermethylation of the *hMLH1* promoter region in HNPCC verus MSI+sporadic colorectal cancers" *J. Med. Genet.*, 2000, 588-592.

Winter, D.B. et al., "Altered spectra of hypermutation in antibodies from mice deficient for the DNA mismatch repair protein PMS2" *Proc. Natl. Acad. Sci.*, USA, Jun. 1998, 95, 6953-6958.

Nicolaides, Nicholas C., et al., "A Naturally Occurring hPMS2 Mutation Can Confer a Dominant Negative Mutator Phenotype," Molecular and Cellular Biology, Mar. 1998, vol. 18, No. 3, pp. 1635-1641.

K.M. Culligan and J.B. Hayes, "DNA Mismatch Repair in Plants," Plant Physiology, American Society of Plant Physiologists, 1997, vol. 115, pp. 833-838.

Lipkin, Steven M., et al., "MLH3: A DNA Mismatch Repair Gene Associated With Mammalian Microsatellite Instability," Nature Genetics, Jan. 2000, vol. 24, No. 1, pp. 27-35.

Jean M, et al., "Isolation and Characterization of AtMLH1, a MulL Homologue from *Arabidopsis thaliana*," Molecular and General Genetics, Dec. 1999, vol. 262, No. 4-5, pp. 633-642.

Chang et al 2001, Genome Research 11(7): 1145-1146.

Pang et al 1997, Molecular and Cellular Biology 17(8): 4465-4473.

* cited by examiner

Figure 1A

```
humPMS2   (1077) GATAGGAATGTTTGATAGTGATGTCAACAAGCTAAATGTCAGTCAGCAGCCACTGCTGGATGTTGAAGGT
AtPMS2    (993)  GAG-GCAAGCTCTGA----------A-CGAGATATATTCC--T------CCAGTAATGCGTCTTATA---
Consensus (1121) GA  GGAA GT TGA          A C AG TA AT  C T      CCA T  TG TTT  A
                 1191                                                                 1260
humPMS2   (1147) AACTAATAAAAATGCATGCAGCCGATTTGGAAAAGCCCATGGTAGAAAAGCAGGATCAATCCCGTTCAT
AtPMS2    (1040) ----TTGTTAATAGGTTCGAGGAGAATTCGGAGCAACC------AGATAAC---CCTGGAGTTTCGTCGT
Consensus (1191)    T  AA A G    G  G GATT GGA A CC      AGA AAG    G  T  A    C TC T
                 1261                                                                 1330
humPMS2   (1217) TAAGGACTGGAGAAGAAAAAAAAGACGTGTCCATTTCCAGACTGCGAGACGCCTTTTCTCTTCGTCACAC
AtPMS2    (1097) TTC-------AGAAGAAATCAAA------TCTTTTGTCAGA-GGGATAC-----TTCTGGATGTCAGTT
Consensus (1261) T         AGAAGAAA  AAA      TC TT  CAGA G GA AG     TTCT    GTCA
                 1331                                                                 1400
humPMS2   (1287) AACAGAGAACAAGCCTCACAGCCCAAAGACTCCAGAACCAAGAAGGAGCCCTCTAGGACAGAAAAGGGGT
AtPMS2    (1148) CTAA----AACAAGACT---AGGGGAAGCTATTGAAAAGAAAATCCATCCTTAAGGAGGTTGAAATTGA
Consensus (1331)  A   AACAAG CT     AG   AA    T  AGAA AA A  ACC T  GGA       AA    G
                 1401                                                                 1470
humPMS2   (1357) ATGCTGTCTTCGTAGCACTTCAGGTGCCATCTCTGACAAAGCCGTCCTGAGACCTCAGAAAGAGGCAGTGA
AtPMS2    (1212) TAATAGTTCGCCAATGAGAAGTTTAAGTTTGAGATCAAGGCATG-TCGGACGA-AGAAAGCGGAAG---
Consensus (1401)        GT  C A     AG T   T T  GA    AAGGC T  TG GAC   AGAAAG GG AG
                 1471                                                                 1540
humPMS2   (1427) GTTCCAGTCACGGACCCAGTGACCCCTACGGACAGAGCGGAGGTGGAGAAGCACTCGGGGCACGGCAGCAC
AtPMS2    (1277) GTTCT--TTAT-----CAGT---CCAT-GATGTAACTCACCTTGACAAG-ACACCTAGCAAAGGTTTGC
Consensus (1471) GTTC  T A     CAGT    CC  GA  A  T GA AAG ACC  GCA  G         C
                 1541                                                                 1610
humPMS2   (1497) TCCGTGGATTCTGAGGGGTTCAGCATCCCAGACACGGGCAGTCACTGCAGCAGCGAGTATGCGGCCAGC
AtPMS2    (1334) CTCACTTAAATGTGACTG------------AGA------AAGTTACTCATCCA---AGTA------AAG
Consensus (1541) TC GT  A T TGA  G            AGA       AGT ACTG GCA    AGTA         A
                 1611                                                                 1680
humPMS2   (1567) TCCCCAGGGGACAGGGCCTCGCAGGAACATGTGGACTCTCAGGAGAAAGCGCCTGAAACTGACGACTCTT
AtPMS2    (1376) ACTTGAC----CAGCCGCTCT----A-GCTTTGCCCAGTCA---------ACTT----TGAATACTTTT
Consensus (1611)  C  AG    CAG GCTC    A  T TG C TCA           CT    TGA  ACT TT
                 1681                                                                 1750
humPMS2   (1637) TTTCAGATGTGGACTGCCATTCAAACCAGGAAGATACCGGATGTAAATTTCGAGTTTTGCCTCAGCCAAC
AtPMS2    (1423) GTTACCATGGG----------AAA-----AAGAAAC-ATGAAAA----------CATAAGC--AC
Consensus (1681) TT  ATG G           AAA      AAGA A C ATG AAA            C T AGC  AC
                 1751                                                                 1820
humPMS2   (1707) TAATCTCGCAACCCCAAAACAAAAGCSTTTTAAAAAAGAAGAAATTCTTTCCAGTTCTGACATTTGTCAA
AtPMS2    (1461) CATCCTCTCTG----AAACACCT---GTCCTCAGAAACCA-AACTTCT----ACTTAT--CGTGTCGAGA
Consensus (1751)  A CTC C    AAACAC   GT  T AAA  A AA TTCT    AGTT T  C T TG   A
                 1821                                                                 1890
humPMS2   (1777) AAGTTAGTAAATACTCAGGACATGTCAGCCTCTCAGCGTTCATGTAGCCTGTGAAAATTAATAAGAAAGTTG
AtPMS2    (1517) AA---AGCAAATTTGAAGTTGCTGC------CTTAGCTTCA---AGGTGT-----CTCGT--GGAAGCG
Consensus (1821) AA   AG AAAT   AG C TG    CT AG TT A   AG TGT     T  T G AAG  G
                 1891                                                                 1960
humPMS2   (1847) TGCCCCTGGACTTTTCTTATGAGTTCTTTAGCTAAACGAATAAAGCAGTTACATCATGAAGCACAGCAAAG
AtPMS2    (1568) ATCAACTTGA---TGATATG-G-----TCATCTCAAAG------GAAGATATGACACCAAGCG----AAAG
Consensus (1891)  C  CT GA    T TATG G      T A CT AA G      G AG TA  CA  AAGC    AAAG
                 1961                                                                 2030
humPMS2   (1917) TGAAGGGGAACAGAATTACAGGAAGTTTAGGGCAAAGATTTGTCCTGGAGAAAATCAAGCAGCCCGAAGAT
AtPMS2    (1620) AGATTCTGAACT-------AGGCAATC---G-----GATTTCTCCTGGAACA---CAAGCTGATAATGTT
Consensus (1961) GA   GAAC    AGG A T    G     GATTT TCCTGGA A  CAAGC G    A G T
                 2031                                                                 2100
humPMS2   (1987) GAACTAAGAAAAGAGATAAGTAAAAGATGTTTGCAGAAATGGAAATCATTCGTCACTTTAACCTGGGAT
AtPMS2    (1672) GAA---AGACATGAGAGA-GTA---C-----------------TCGGCAATTCAATCTTCGGT
Consensus (2031) GAA   AGA A GAGA A GTA   C                          T GG CA TT AA CT GG T
                 2101                                                                 2170
humPMS2   (2057) TTATAATAAGCCAAACTGAATGAGGATATCTTCATAGTGGACCAGCATGCCACCGACGAGAAGTTATAACTT
AtPMS2    (1712) TCATCATTGCAAAATGGAGCGAGATCTGTTCATTGTGGATCAGCATGCAGCTGATGAGAAATTCAACTT
Consensus (2101) T AT AT  C AAA TG A   GAT T TTCAT GTGGA CAGCATGC  C GA GAGAAA T  AACTT
                 2171                                                                 2240
humPMS2   (2127) CGAG-ATGCTGCAGCAGCACACCGTGCCTCCAGGGGCAGAGGCTCATAGCA-CCTCAGACTCTCAACTTAA
AtPMS2    (1782) CGAACATTTAGCAAGGTCA-ACTGTCCTGAACCAGCA-ACCCTTACTCCAGCCTTTGAACTTGGACTCT
Consensus (2171) CGA  AT  GCA     CA AC GT CT    GCA A CT A  CA CCT GA   T   A  T
                 2241                                                                 2310
humPMS2   (2195) CTGCTGCTTAATGAAGCTGTTCTGATAGAAAATCTGAAATATTTAGAAAGAATGGCTTTGATTTTGTTAT
AtPMS2    (1850) CTCCAGAAGAAGAAGTAACTGTGTTAATGCACATGGATATTATCAGGAAAATGGCTTTCTTCTACAGGA
Consensus (2241) CT C G  A GAAG   T TG TA  A  TGGA AT  AG A AATGGCTTT   T   T G
                 2311                                                                 2380
```

Figure 1B

```
humPMS2    (2265) CGATGAAAATGCTCCAGTCACTCAAAGGGCT--AAACTGATTTCCTTGCCAACTAGTAAAAACTGGACCT
AtPMS2     (1920) GAATCCAAGTGCTCC--TCCCGGAAAACACTTTAGACTACGAGCCATTCCTTATAGCAAGAATATCACCT
Consensus  (2311)    AT  AA TGCTCC  TC C GAAA   CT  A ACT      CC T CC   TAG AA AA    ACCT
                 2381                                                                   2450 humPMS2    (2333) TCGGACCCCAGGACGTCGATGAACTGATCTTCATGCTGAGCGACAGCCCTGGGG-----TCATGTGCCGG
AtPMS2     (1988) TTGGAGTCGAAGATCTTAAAGACCTGATCTCAACTCTAGGAGATAACCATGGGGAATGTTCGGTTGCTAG
Consensus  (2381) T GGA  C A GA  T  A GA CTGATCT  A  CT  G GA A CC TGGGG     TC   TGC G
                 2451                                                                   2520 humPMS2    (2398) ------------------------------------CCTTCCCGAGTCAAGCAGATGTTTGCCTCCAGAGCC
AtPMS2     (2058) TAGCTACAAAACCAGCAAAACAGATTCGATTTGTCCATGACGAGTCCGTGCAATGCTAGCATCCCGAGCA
Consensus  (2451)                                     CC TC CGAGTC    ATG T GC TCC GAGC
                 2521                                                                   259 humPMS2    (2434) TGCCCGAAGTCGGTGATGATTGGGACTGCTCTTAACACAAGCGAGATCAACAAACTGATCACCCACATGG
AtPMS2     (2128) TGCAGATCATCTGTGATGATCGGAGATCCACTCAGAAAAACGAAATGCAGAAGATAGTAGAACACTTGG
Consensus  (2521) TGC G    TC GTGATGAT GG    T  CT A  A  AA CGA ATG AGAA  T  T   CAC TGG
                 2591                                                                   2660 humPMS2    (2504) GGGAGATGGACCACCCCTGGAACTGTCCCCATGGAAGGCCAACCATGAGACACATCGCCAACCTGGGTGT
AtPMS2     (2198) CAGATCTCGAATCTCCTTGGAATTGCCCACACGGACGACCAACAATGCGTCATCTTGTGGACTTGACAA-
Consensus  (2591)    GA T GA   CC TGGAA TG CC CA GGA G CCAAC ATG G CA   T G   AC TG
                 2661                                                                   2730 humPMS2    (2574) CATTTCTCAGAAC-------------------------------------------------------
AtPMS2     (2267) CTTTACTCACATTACCTGATGACGACAATGTCAATGATGATGATGATGATGCAACCATCTCATTGGC
Consensus  (2661) C TT CTCA A                                                         
                 2731 humPMS2    (2587) ----
AtPMS2     (2337) ATGA
Consensus  (2731)
```

```
              1                                                                    70
humPMS2    (1) ----------MERAESSST----EPAKAIKPIDRKSVHQICSGQVVLSLSTAVKELVENSLDAGATNIDL
AtMLH1     (1) MIDDSSLTAEMEEESPATTIVPREPPKIQRLEESVNRIAAGEVIQRPVSAVKELVENSLDADSSSTSV
Consensus  (1)           ME  ES AT       I  ID  V  I AG VI   SAVKELVENSLDA AS I L
              71                                                                   140
humPMS2   (57) KLKDYGVDLIEVSDNGCGVEEENFEGLTLKHHTSKIQEEADLTQVETFGFRGEALSSLCALSDVTISTCH
AtMLH1    (71) VVKLGGLKLIQVSDDGHGIRREDLPILCERHTSKLTKFEDIFSLSSMGFRGEALASMTYVAHVTVTTIT
Consensus (71) LKD GL LI VSD G GI E   L KH TSKI   F DL  S  GFRGEALASL  LA VTIST
              141                                                                  210
humPMS2  (127) ASAKVGTRLMFDHNGKIIQKTPYPRPRGTTVSVQQLESTLPVRHKEFQRNIKKEYAKMVQVLHAYCIISA
AtMLH1   (141) KGQIHGYRVSYRDGVMEHEPKACAAVKGTQIMVENLFYNMIARRRTLQ-NSADDYGKIVDLLSRMAIHYN
Consensus(141)      G  RL F              KGT I V NLF  L R K  Q N   DYAKIV LL    I
              211                                                                  280
humPMS2  (197) GIRVSCTNQLGQGKRQPVVCTGGSPSIKENTGSVFGQKQLQSLIPFVQLPPSDSVCEEYGLSCSDALHNL
AtMLH1   (210) NVSFSCRKH---GAVKADVHSVVSPSRLDSIRSVYGVSVAKNLM---KV--E--------VSSCDSSGCT
Consensus(211)    I  SC    G    V S SPS  D I SVFG      LI  L              LS DA
              281                                                                  350
humPMS2  (267) GYISGFISQCTHGVGRSSTDRQFFFINRRPCDPAKVCRLVNEVYHM-YNRHQYPFVVLNISVDSECVDIN
AtMLH1   (264) FDMEGFISNSNYVAKKTIL---VLFINDRLVECSALKRATEIVYAATLPKASKPFVYMSINLPRDHVDIN
Consensus(281) F I GFISN  H   KS       FIN R   DALRI VY     K   PFV L I  E VDIN
              351                                                                  420
humPMS2  (336) VTEDKRQILLQEEKLLLAVLKTSLIGMFDSDVNKLNVSQQPLLDVEGNLIKMHAADLEKPMVEKQDQSPS
AtMLH1   (331) IHETKKEVSLLNQEIIIEMIQ---------------SEVE--------VKLRNANDTRTFQEQKVEYIQ
Consensus(351) I  P KK I L   III MI                S           IKL  A   K  E
              421                                                                  490
humPMS2  (406) LRTGEEKKDVSISRLREAFSLRHTTENKEHSPKTPEPRRSPLGQKRGMLSSSTSGAISDKGVLRPQKEAV
AtMLH1   (377) STLTSQKSDSPVSQKPSG----QKIQKVEVNKMVRTDSSDEAGRLHAFLQPKPQSLPDKVSSLSVVRSSV
Consensus(421)        KD  IS  A        T     P       PG  AL       L   K AV
              491                                                                  560
humPMS2  (476) SSSHGESDPTDRAEVEKDSGHGSTSVDSEGFSIPDTGSHCSSEYAASSPGDRGSQEHVDSQEKAPETDDS
AtMLH1   (443) RQRRNPKETADLSSVQE---------------LIA--G------V-DSCCHPGMLETVRNCTYVGMADDV
Consensus(491)      PD DAV                   I           S  G  E V         DD
              561                                                                  630
humPMS2  (546) ESDVDCHSNQEDTGCKFRVLPQPTNLATPNTKRFKKEEILSSSDICQKLVNTQDMSASQVDVAVKINKKV
AtMLH1   (489) EALVQYN-----IHLYLAN-------VVNLSKELMYQQTLRRFAHFNAIQLSDPAPLSELILLALKEEDL
Consensus(561) FA V       T          SK    L       NI S    SLL        L
              631                                                                  700
humPMS2  (616) VELDFSMSSLAKRIKQLHHPAQQSEGFQNYRKFRAKICPGENQAAEDELRKEISKTMFAEMEIIGQFNLG
AtMLH1   (547) DPGNDTKDDIKERIAEMNTPLLKEKAPMLEEYSVHIDSSANLSRLPVILDQYTPDMDRVPEFL--LCLG
Consensus(631)  P    S    L  RI LE    AE   F   I       NA  I     S M   EI    LG
              701                                                                  770
humPMS2  (686) FIITKLNEDIFIVDQHATDEKYNFEMLQQHTVLCQRLIAPQTLNLTAVNEAVLIENLEIFRKNGFDFVI
AtMLH1   (615) NDVEWEDEKSCFQGVSAAIGNFYAMHPPLLPNPSGDGIQFYSKRGESSQEKSDLEGNVDMEDNLDQLLS
Consensus(701)    I    E       A  F           G I         SA  AL   NLDI    D L
              771                                                                  840
humPMS2  (756) DENAPVTEEAKLISLPTSKNATFGPQDVDELIFMLSDSPGVMCRPSRVKQMFASRACRKSVMIGTALNTS
AtMLH1   (685) DAENAWAQE---------BWSIQHVLFPSMRLELKPPASMASNGTFVKVASLEKLYKIFERC-------
Consensus(771) D      R         WS     L       L      M   S VK       K  K
              841             877
humPMS2  (826) EMKKLITHMGEMDHPWNCPHGRPTMRHIANLGVISQN
AtMLH1   (738) ------------------------------------
Consensus(841)
```

Figure 3

```
                    1                                                                70
humPMS2      (1)    MERAESSSTEPAKAIKPIDRKSVHQICSGQVVLSLSTAVKELVENSLDAGATNIDLKLKDYGVDLIEVSD
AtPMS1       (1)    ----------MKTIKPLPEGVRESMRSGIIMFDMARVEELVFNSLDAGATKVSIFVGVVSCS-VKVVD
Consensus    (1)              K IKPI   H ISG IM  LA V ELV NSLDAGAT I IL         I V D
                    71                                                               140
humPMS2      (71)   NGCGVEEENFEGLTLKHHTSKIQEFADL-TQVETFGFRGEALSSLCALSDVTISTCHASAKVCTRLMFDH
AtPMS1       (59)   DGSGVSRDDLVLLGERYATSKFHDETNVETASETFGFRGEALAISDISLLEVRTKAIGRPNGYRKVMKG
Consensus    (71)    G GV      D    L KH TSK   DF  T  ETFGFRGEALASI IS LIT            GRM
                    141                                                              210
humPMS2      (140)  NGKIIQKTPYPRP-RGTTVSVQQLFSTLPVRHKEFQRNIKKEYAKMVQVLHAYCIISAGI----------
AtPMS1       (129)  SKCLHLGIDDDRKDSGTTVTVRDLFYSQPVRRKYMQSSPRKVLESIKKCVFRIALVHSNVSFSVLDIESD
Consensus    (141)    I   R      GTTVSV  LF S PVR K Q    KK  I L          II A I
                    211                                                              280
humPMS2      (199)  ----------------------------------RVSCTNQLGQGKRQPVVCTGGSPSIKENIGSV
AtPMS1       (199)  EELFQTNPSSSAFSLLMRDAGTEAVNSLCKVNVTDGMLNVSGFECADDWKPTDGQQTGRRNRLQSNPGYI
Consensus    (211)                                    VS             K    TG       I N GI
                    281                                                              350
humPMS2      (231)  -------------EGQKQLQSLIPEVQLPESDSVCEEYGLSCSDALHNLFYISGFISQCTHGVGRSSTDRQF
AtPMS1       (269)  LCIACPRRLYEESFEPSKTHVEEKKWGEVLAFIERITLANWKKDRILELFDGGADILAKCDRQDLIDKI
Consensus    (281)                 F    SIF   PAE LA       LG     G       D
                    351                                                              420
humPMS2      (290)  FFINR--------------RPCDPAKVCRLVNEVYHMYNRHQYPFVVLNISVDSECVDINVTPDKRQILI
AtPMS1       (339)  RLQNGSLFSILHFLDADWPEAMEPAKKKLKRSNDHAPCSSLLFPSADFKQDGDYFSPRKDVWSPECEVEL
Consensus    (351)     N              DPAK      H        FP       D     V           I L
                    421                                                              490
humPMS2      (346)  QEEKLLLAVLKTSLIGMFDSDVNKLNVSQQPLLDVEGNLIKMHAADLEKPMVEKQDQSPSLRTGEEKKDV
AtPMS1       (409)  KIQNPKEQGTVAGFESRTDSLLQSRDIEMCTNEDFPQVTDLLETSLVADSKCRKQFLTRCQITPVNINH
Consensus    (421)                    DS LN  I Q D    L AL         KQ  S   T
                    491                                                              560
humPMS2      (416)  SISRLREAFS---------------------------------LRITTENKPHSPKTEEPRRSPLGQ
AtPMS1       (479)  DFMKDSDVLNFQFQGLKDELDVSNCIGKHLLRGCSSRVSLTFHEPKLSHVEGYESVVPMIENEKQSSPRV
Consensus    (491)    K D                                       L H        P  P KS
                    561                                                              630
humPMS2      (450)  KRGMLSSSTSGAISDKGVLRPQKEAVSSSHG--ESDPTDRAEVEKDSGHGSTSVDSEGGSIPDTGSHCSS
AtPMS1       (549)  LETREGGSYCDVYSDKTPDCSLGSSWQDTDWFTEQCSSDRGCVGIGEDFNITPIDTAEEDSYDEKVGSKK
Consensus    (561)        S     SDK       A  S       P   SDRA V      T  IDS  F  D
                    631                                                              700
humPMS2      (518)  EYAASSPGDRGSQEHVDSQE-----KAPETDDSFSDVDCHSNQEDTGCKFRVLEQETNLATPNTKRFKKE
AtPMS1       (619)  YLSSVNVGSSVTGSFCLSSEWSPMYSTESATKWESEYQKGCRILEQSLRLGRMEDEEFCFSAANNIKFDH
Consensus    (631)     AA  G   S    S  E         P         SD    D  K   LP P  S
                    701                                                              770
humPMS2      (583)  EILSSSDICQKLVNTQDMSASQVDVAVKINKK----VVPLDFSMSSLAKRIKQLHHEACQSEGEQNYRKF
AtPMS1       (689)  EVIPEMDCCETGTDSFTAIQNCTQLADKTCKSSWGHADDVRIDQYSIRKEKFSYMDGTQNNAGKQRSKRS
Consensus    (701)  EII   D C     S            LA KI K      L        SI K      QN G Q  KK
                    771                                                              840
humPMS2      (649)  RAKICPGENQ---------------------------------------------------------
AtPMS1       (759)  RSAPPFYREKKRFISLSCKSDTKPKNSDPSEPDDLECLTQPCNASQMHLKCSILDDVSYDHIQETEKRLS
Consensus    (771)  RA
                    841                                                              910
humPMS2      (659)  ---------------------------------------------------------------------
AtPMS1       (829)  SASDLKASAGCRTVHSETQDEDVHEDFSSEEFLDPIKSTTKWRHNCAVSQVPKESHELHGQDGVFDISSG
Consensus    (841)
                    911                                                              980
humPMS2      (659)  -----AAEDELRKEISKTMFAEMEIIGQFNLGFIITKLNEDIFIVDQHATDEKYNFEMLQQHTVLQGQRL
AtPMS1       (899)  LLHLRSDESLVPESINRHSLEDAKVLQQVDKKYTPIVACGTVAIVDQHAADERIRLEELRTKFINDALLI
Consensus    (911)       A E L  IK    D  II Q     FI      I IVDQHA DEK   E L    I A I
                    981                                                              1050
humPMS2      (724)  IAPQTLNLTAVNEAVLIENLEIFRKNGFDFVIDENAPVTERAK-----------LISLPTSKNWTFGPQ
AtPMS1       (969)  FVLTLKVLPEMGYQLLQSYSEQIRDWGWICNETVEGSTSFKKNMSIIQRKPTPITQNAVPCILGVNLSDV
Consensus    (981)        L  M  LL    E  RGF I    A SK              L ALP
                    1051                                                             1120
humPMS2      (782)  DVDFLIFMLSDSPGVMCRPSRVKQMFASRACRKSVMIGTALNTSEMKKLITHMGEMDHPWNCPIGRPTMR
AtPMS1       (1039) DLLEFLQQLADTDGSSTIPPSVLRVLNSKACRGAIMFGDSLLPSECSLITDGLKQTSLCFQCAHGRPTTV
Consensus    (1051) DL E I LADS G    P SV  V M  SKACR AIM G AL  SE   II L      FNC HGRPT
                    1121               1164
humPMS2      (852)  HIANLGVISQN--------------------------
AtPMS1       (1109) PLVDDKALHKQIAKLSGRQVWHGLQRREITLDRAKSRLDNAKS-
Consensus    (1121) I L  I N
```

Figure 4

```
              1                                                              70
humPMS134  (1) ATGGAGCGAGCTGAGAGCTCGAGTACAGAACCTGCTAAGGCC------ATCAAACCTATTGATCGGAAGT
AtPMS134   (1) ATGCAAGGAGATTCTTCTCCGTCTCCGACGACTACTAGCTCTCCTTTGATAAGACCTATAAACAGAAACG
Consensus  (1) ATG A  GAG T       CG T C    CT CTA  C       AT A ACCTAT  A  GAA
              71                                                             140
humPMS134 (65) CAGTCCATCAGATTTGCTCTGGGCAGGTGGTACTGAGTCTAAGCACTGCGGTAAAGGAGTTAGTAGAAAA
AtPMS134  (71) TAATTCACAGAATCTGTTCCGGTCAAGTCATCTTAGACCTCTCTTCGGCCGTCAAGGAGCTTGTCGAGAA
Consensus (71)  A T CA   AT TG TC GG CA GT T  T    CT     C GC GT AAGGAG T GT GA GAA
              141                                                            210
humPMS134 (135) CAGTCTGGATGCTGGTGCCACTAATATTGATCTAAAGCTTAAGGACTATGGAGTGGATCTTATTGAAGTT
AtPMS134 (141) TAGTCTCGACGCCGGCGCCACCAGTATAGAGATTAACCTCCGAGACTACGGCGAAGACTATTTTCAGGTC
Consensus (141)  AGTCT GA GC GG GCCAC A TAT GA  T AA CT    GACTA GG G  GA   T TT A GT
              211                                                            280
humPMS134 (205) TCAGACAATGGATGTGGGGT----------AGAAGAAG---------AAAACTTCGAAGG-CTTAA-
AtPMS134 (211) ATTGACAATGGTTGTGGCATTTCCCCAACCAATTTCAAGGTTTGTGTCCAAATTCTCCGAAGAACTTTTG
Consensus (211)    GACAATGG TGTGG  T          A      AAG        AA   CT CGAAG  CTT
              281                                                            350
humPMS134 (251) --------CTCTGAAACATCACACATCTAAGATTCAAGAGTTTGCCGACCTAACTCAGGTTGAA-ACTT
AtPMS134 (281) ATGTTCTTGCACTTAAGCATCATACTTCTAAATTAGAGGATTTCACAGATCTTT-TGAATTTGACTACTT
Consensus (281)         C CT AA CATCA AC TCTAA T A GA TT  C GA CT    T A TTGA ACTT
              351                                                            420
humPMS134 (311) TTGGCTTTCGGGGGGAAGCTCTGAGCTCACTTTGTGCACTGAGCGATGTCACCATTTCTAGCCTC--CCAC
AtPMS134 (350) ATGGTTTTAGAGGAGAAGCCTTGAGCTCTCTCTGTGCATTGGGAAATCTCACTGTGGAAACAAGAACAAA
Consensus (351)  TGG TTT G GG GAAGC  TGAGCTC CT TGTGCA TG G  AT TCAC T   AC  G   C A
              421              444
humPMS134 (379) GCATCGGCGAAGGTTGGAACT---
AtPMS134 (420) GAATGAGCCA--GTTGCTACGCTC
Consensus (421) G AT GC A  GTTG  AC
```

Figure 6

```
                 1                                                                    70
humPMS134    (1) --MERAESSSTEPAKAIKPIDRKSVHQICSGQVVLSLSTAVKELVENSLDAGATNIDLKLKDYGVDLIEV
AtPMS134     (1) MQGDSSPSPTTTSSPLIRPINRNVIHRICSGQVILDLSSAVKELVENSLDAGATSIEINLRDYGEDYFQV
Consensus    (1)    D A S ST  A   IKPI R  IH ICSGQVIL LSSAVKELVENSLDAGAT IDI LKDYG D   V
                 71                                                                  140
humPMS134   (69) SDNGCGVEEENF-----------EGLTLKHHTSKIQEFADLTQVETFGFRGEALSSLCALSDVTISTCHA
AtPMS134    (71) IDNGCGISPTNFKVCVQILRRTFDVLALKHHTSKLEDETDLLNLTTYGFRGEALSSLCALGNLTVETRTK
Consensus   (71)  DNGCGI    NF              D L LKHHTSKI DF DL NL T GFRGEALSSLCAL   LTI T
                 141
humPMS134  (128) SAKVGT
AtPMS134   (141) NEPVATL
Consensus  (141)    VAT
```

Figure 7

METHOD FOR GENERATING HYPERMUTABLE PLANTS

TECHNICAL FIELD OF THE INVENTION

The invention is related to the area of mismatch repair genes. In particular it is related to the field of mutagenesis.

BACKGROUND OF THE INVENTION

Within the past four years, the genetic cause of the Hereditary Nonpolyposis Colorectal Cancer Syndrome (HNPCC), also known as Lynch syndrome II, has been ascertained for the majority of kindreds affected with the disease (1). The molecular basis of HNPCC involves genetic instability resulting from defective mismatch repair (MMR). To date, six genes have been identified in humans that encode proteins which appear to participate in the MMR process, including the mutS homologs GTBP, hMSH2, and hMSH3 and the mutL homologs hMLH1, hPMS1, and hPMS2 (2-7). Germline mutations in four of these genes (hMSH2, hMLH1, hPMS1, and hPMS2) have been identified in HNPCC kindreds (2-7). Though the mutator defect that arises from the MMR deficiency can affect any DNA sequence, microsatellite sequences are particularly sensitive to MMR abnormalities (8,9). In addition to its occurrence in virtually all tumors arising in HNPCC patients, Microsatellite Instability (MI) is found in a small fraction of sporadic tumors with distinctive molecular and phenotypic properties (10).

HNPCC is inherited in an autosomal dominant fashion, so that the normal cells of affected family members contain one mutant allele of the relevant MMR gene (inherited from an affected parent) and one wild-type allele (inherited from the unaffected parent). During the early stages of tumor development, however, the wild-type allele is inactivated through a somatic mutation, leaving the cell with no functional MMR gene and resulting in a profound defect in MMR activity. Because a somatic mutation in addition to a germ-line mutation is required to generate defective MMR in the tumor cells, this mechanism is generally referred to as one involving two hits, analogous to the biallelic inactivation of tumor suppressor genes that initiate other hereditary cancers. In line with this two-hit mechanism, the non-neoplastic cells of HNPCC patients generally retain near normal levels of MMR activity due to the presence of the wild-type allele (11-12).

While MMR is a conserved process found in bacteria, yeast and mammalian cells (14-16), its activity has not been confirmed in plants. While sequences homologous to MMR genes have been identified in *Arabidopsis thaliana*, it is not known if they are functional in plants in the process of MMR (17-18). There is a need in the art for identification of the processes involved in genome stability in plants. There is a continuing need for methods and techniques for generating genetic diversity in agriculturally important crops.

SUMMARY OF THE INVENTION

It is an object of the invention to provide a method for making a hypermutable cell.

It is another object of the invention to provide a homogeneous composition of cultured, hypermutable, plant cells.

It is still another object of the invention to provide a hypermutable transgenic plant.

It is yet another object of the invention to provide a method for generating a mutation in a gene of interest in a plant cell.

It is still another object of the invention to provide a method for generating a mutation in a gene of interest in a plant.

It is an object of the invention to provide a method for generating a hypermutable plant.

It is another object of the invention to provide a vector for introducing a dominant negative MMR allele into a plant.

It is even another object of the invention to provide an isolated and purified polynucleotide encoding a plant MutL homolog.

It is another object of the invention to provide an isolated and purified protein which is a plant MutL homolog.

It is an object of the invention to provide a method for determining the presence of a mismatch repair (MMR) defect in a plant or a plant cell.

These and other objects of the invention are provided by one or more of the following embodiments. In one embodiment of the invention a method for making a hypermutable cell is provided. A polynucleotide comprising a dominant negative allele of a mismatch repair gene is introduced into a plant cell, whereby the cell becomes hypermutable.

In another aspect of the invention a homogeneous composition of cultured, hypermutable, plant cells is provided. The plant cells comprise a dominant negative allele of a mismatch repair gene.

Another aspect of the invention is a hypermutable transgenic plant. At least 50% of the cells of the plant comprise a dominant negative allele of a mismatch repair gene.

According to another aspect of the invention a method is provided for generating a mutation in a gene of interest in a plant cell. A hypermutable plant cell comprising the gene of interest and a dominant negative allele of a mismatch repair gene is grown. The cell is tested to determine whether the gene of interest harbors a newly acquired mutation.

Another embodiment of the invention is a method for generating a mutation in a gene of interest in a plant. A plant comprising the gene of interest and a polynucleotide encoding a dominant negative allele of a mismatch repair gene is grown. The plant is tested to determine whether the gene of interest harbors a newly acquired mutation.

According to another aspect of the invention a method is provided for generating a hypermutable plant. Endogenous mismatch repair (MMR) activity of a plant is inhibited. The plant becomes hypermutable as a result of the inhibition.

Another aspect of the invention is a vector for introducing a dominant negative MMR allele into a plant. The vector comprises a dominant negative MMR allele under the transcriptional control of a promoter which is functional in a plant.

Still another aspect of the invention provides an isolated and purified polynucleotide encoding *Arabidopsis thaliana* PMS2 as shown in SEQ ID NO: 12.

Another aspect of the invention provides an isolated and purified polynucleotide encoding *Arabidopsis* PMS134 as shown in SEQ ID NO: 14.

According to another embodiment of the invention an isolated and purified protein which is *Arabidopsis* PMS2 is provided. It has the amino acid sequence as shown in SEQ ID NO: 12.

Another embodiment of the invention is an isolated and purified protein which is *Arabidopsis* PMS134. It has the amino acid sequence as shown in SEQ ID NO: 14.

Still another aspect of the invention provides a method for determining the presence of a mismatch repair (MMR) defect in a plant or a plant cell. At least two microsatellite markers in test cells or a test plant are compared to the at least two microsatellite markers in cells of a normal plant. The test plant or plant cells are identified as having a mismatch repair defect if at least two microsatellite markers are found to be rearranged relative to the cells of the normal plant.

BRIEF DESCRIPTION OF THE DRAWINGS

FIGS. 1 A-C. Alignment of the *Arabidopsis thaliana* and human PMS2 cDNAs (SEQ ID NOS: 4 and 3, respectively). Similarity is 48.1%; identity is 48.1%. Black boxes show identical nucleotides.

FIG. 2. Alignment of the *Arabidopsis thaliana* and human PMS2 proteins (SEQ ID NOS: 11 and 12, respectively). Similarity is 41.5%; identity is 31.1%. Black boxes show identical residues.

FIG. 3. Alignment of the *Arabidopsis thaliana* MLH1 homolog and the human PMS2 proteins (SEQ ID NOS: 9 and 11, respectively). Similarity is 30%; identity is 18.4%. Black boxes show identical residues.

FIG. 4. Alignment of the *Arabidopsis thaliana* PMS1 homolog and the human PMS2 proteins (SEQ ID NOS: 10 and 11, respectively). Similarity is 24.4; identity is 15%. Black boxes show identical residues.

FIG. 6. Alignment of the *Arabidopsis thaliana* PMS134 and the human PMS134 cDNA (SEQ ID NOS: 6 and 5, respectively). Similarity is 24.4%; identity is 15%. Black boxes show identical residues.

FIG. 7. Alignment of the *Arabidopsis thaliana* PMS134 and the human PMS134 polypeptide (SEQ ID NOS: 14 and 13, respectively). Similarity is 65.1%; identity is 50.7%. Black boxes show identical residues.

DETAILED DESCRIPTION OF THE INVENTION

Figure 5:
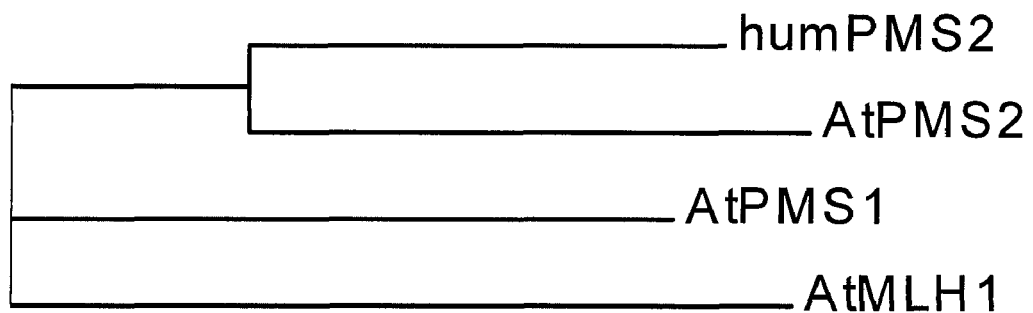
FIG. 5. Phylogenetic tree of *Arabidopsis thaliana* MutL homologs and the human PMS2 protein.

It is a discovery of the present inventors that plant cells have functional mismatch repair (MMR) systems which function similarly to mammalian MMR. Moreover, dominant negative alleles can be made and used to generate variability in plants and plant cells, as in mammalian cells. Other means of interfering with normal MMR activity can also be used as described in detail below. Dominant negative alleles of mismatch repair genes, when introduced into cells or plants, increase the rate of spontaneous or induced mutations by reducing the effectiveness of DNA repair and thereby render the cells or whole organism hypermutable. Hypermutable plant cells or plants can be utilized to develop new mutations in a gene of interest.

The process of mismatch repair, also called mismatch proofreading, is carried out by protein complexes in cells ranging from bacteria to mammalian cells (9, 14-16). A mismatch repair (MMR) gene is a gene that encodes one of the proteins of a mismatch repair complex. Although not wanting to be bound by any particular theory or mechanism of action, a mismatch repair complex is believed to detect distortions of a DNA helix resulting from non-complementary pairing of nucleotide bases. The non-complementary base on the newer DNA strand is excised, and the excised base is replaced with the appropriate base, which is complementary to the older DNA strand. In this way, cells eliminate many mutations which occur as a result of mistakes in DNA replication.

For purposes of example, this application discloses use of dominant negative alleles of MMR genes as a method for blocking or inhibiting MMR activity in plants. (Blocking or inhibiting are used synonymously herein, and denote any significant level of inhibition. They do not connote complete inhibition, although the terms include that possibility within their ambit.) However, any molecular method known by those skilled in the art to block MMR gene expression and/or function can be used, including but not limited to gene knockout (19), antisense technology (20), double stranded RNA interference (21), and polypeptide inhibitors (22).

Dominant negative alleles cause a mismatch repair defective phenotype even in the presence of a wild-type allele in the same cell. An example of a dominant negative allele of a mismatch repair gene is the human gene hPMS2-134, which carries a truncation mutation at codon 134 (13, U.S. Pat. No. 6,146,894). The mutation causes the product of this gene to prematurely terminate at the position of the 134th amino acid, resulting in a shortened polypeptide containing the N-terminal 133 amino acids. Such a mutation causes an increase in the rate of mutations which accumulate in cells after DNA replication. Expression of a dominant negative allele of a mismatch repair gene results in impairment of mismatch repair activity, even in the presence of the wild-type allele. Any allele which produces such effect can be used in this invention.

Dominant negative alleles of a mismatch repair gene can be obtained from the cells of humans, animals, yeast, bacteria, plants or other organisms as described by Nicolaides et. al. (23) and Hori et. al. (24). Alternatively such alleles can be made from wild-type alleles, typically by inserting a premature stop codon or other mutation which leads to a protein product which is able to complex with other members of the MMR complex but which is not functional. Such alleles can be identified by screening cells for defective mismatch repair activity. The cells may be mutagenized or not. Cells from plants exposed to chemical mutagens or radiation, e.g., can be screened for defective mismatch repair. Genomic DNA, a plasmid containing cDNA, or mRNA from any cell encoding a mismatch repair protein can be analyzed for variations from the wild type sequence. Dominant negative alleles of a mismatch repair gene can also be created artificially, for example, by producing variants of the hPMS2-134 allele or other mismatch repair genes (13, U.S. Pat. No. 6,146,894). Other truncated alleles of PMS2 or other MMR genes can be made. Such alleles are expected to behave similarly to hPMS2-134. An of various forms of site-directed mutagenesis can be used. The suitability of such alleles, whether natural or artificial, for use in generating hypermutable cells or plants can be evaluated by testing the mismatch repair activity caused by the allele in the presence of one or more wild-type alleles, to determine if the allele is dominant negative.

A cell or a plant into which a dominant negative allele of a mismatch repair gene has been introduced will become hypermutable. This means that the mutation rate (spontaneous or induced) of such cells or plants is elevated compared to cells or plants without such alleles. The degree of elevation of the mutation rate can be at least 2-fold, 5-fold, 10-fold, 20-fold, 50-fold, 100-fold, 200-fold, 500-fold, or 1000-fold that of the normal cell or plant.

According to one aspect of the invention, a polynucleotide encoding a dominant negative form of a mismatch repair protein is introduced into a cell or a transgenic plant. The gene can be any dominant negative allele encoding a protein which is part of a mismatch repair complex, for example, mutS or mutL homologs of the bacterial, yeast, fungal, insect, plant, or mammalian genes. The dominant negative allele can be naturally occurring or made in the laboratory. The polynucleotide can be in the form of genomic DNA, cDNA, RNA, or a chemically synthesized polynucleotide. The polynucleotide can be introduced into the cell by transfection.

Transfection is any process whereby a polynucleotide is introduced into a cell. The process of transfection can be carried out in a living plant, e.g., using a binary vector for gene transmission, or it can be carried out in vitro, e.g., using a suspension of one or more isolated cells in culture. The cell can be any type of plant cell.

In general, transfection can be carried out using a suspension of cells, or a single cell, but other methods can also be used as long as a sufficient fraction of the treated cells incorporates the polynucleotide to allow transfected cells to be readily isolated. The protein product of the polynucleotide may be transiently or stably expressed in the cell. Techniques for transfection are well known in the art of plant cell science. Available techniques for introducing polynucleotides include but are not limited to electroporation, transduction, *Agrobacterium*-mediated gene transfer, cell fusion, the use of calcium chloride, and packaging of the polynucleotide together with lipid for fusion with the cells of interest. Once a cell has been transfected with the mismatch repair gene, the cell can, e.g., be grown and reproduced in culture. If the transfection is stable, such that the gene is expressed at a consistent level for many cell generations, then a cell line results. Alternatively, a dominant negative MMR protein can be directly introduced by microinjection into a cell in order to inhibit MMR activity of the cell.

Root explants are incubated in 0.5 ug/ml of 2-4-dochlorophenoxy-ace-tic acid (2-4D) plus N6-Benzyl-Adenine in growth medium. After 4 weeks, suspension cells are isolated and digested with hemicellulase for protoplast preparation and transfection. Such isolated cells are typically cultured in the absence of other types of cells. Cells selected for the introduction of a dominant negative allele of a mismatch repair gene may be derived from a multicellular plant in the form of a primary cell culture or an immortalized cell line, or may be derived from suspensions of single-celled plants.

A polynucleotide encoding a dominant negative form of a mismatch repair protein can be introduced into the genome of a plant to form a transgenic plant. The plant can be any species for which suitable techniques are available to produce transgenic plants. For example, transgenic plants can be prepared from domestic agricultural crops, e.g. corn, wheat, soybean, rice, sorghum, barley, etc.; from plants used for the production of recombinant proteins, e.g., tobacco leaf; or experimental plants for research or product testing, e.g., *Arabidopsis*, pea, etc. The introduced polynucleotide may encode a protein native to the species or native to another species, whether plant, animal, bacterial, or fungal, for example.

Any method for making transgenic plants known in the art can be used. According to one process of producing a transgenic plant, the polynucleotide is transfected into the plant seedling The seed is germinated and develops into a mature plant in which the polynucleotide is incorporated and expressed. An alternative method for producing transgenic plants involves introducing the polynucleotide into the growing or mature plant by injection, electroporation, *Agrobacterium*-mediated transfer or transfection. With this method, if the polynucleotide is not incorporated into germline cells, the gene will not be passed on to the progeny. Therefore, a transgenic plant produced by this method will be useful to produce products from that individual plant.

To identify whether a gene was inserted into the germline, seedlings derived from such plants can be screened for the transgene. Genetic modification of a growing or mature plant is useful for evaluating the expression of hypermutable constructs and for evaluating effects on altering endogenous mismatch repair. Once transgenic plants are produced, they can be grown to produce and maintain a crop of transgenic plants.

Once a transfected cell line or a crop of transgenic plants has been produced, it can be used to generate new mutations in one or more gene(s) of interest. A gene of interest can be any gene naturally possessed by the cell line or transgenic plant or introduced into the cell line or transgenic plant. An advantage of using MMR-defective cells or plants to induce mutations is that the cell or plant need not be exposed to mutagenic chemicals or radiation, which may have secondary harmful effects, both on the object of the exposure and on the workers.

Mutations can be detected by analyzing the genotype of the cells or plants, for example by examining the sequence of genomic DNA, cDNA, messenger RNA, or amino acids associated with the gene of interest. Mutations can also be detected by testing a phenotype caused by the gene. A mutant phenotype can be detected, e.g., by identifying alterations in electrophoretic mobility, spectroscopic properties, or other physical or structural characteristics of a protein encoded by a mutant gene. One can also screen for altered function of the protein in situ, in isolated form, or in model systems. One can screen for alteration of any property of the cell or plant associated with the function of the gene of interest or its protein product. Finally, one can screen for macroscopic phenotypes such as but not limited to color, height, or the ability to grow in drought, high-salt, cold, hot, acidic, basic, pest-infested, or high ethylene environments.

The above disclosure generally describes the present invention. A more complete understanding can be obtained by reference to the following specific examples that will be provided herein for purposes of illustration only, and are not intended to limit the scope of the invention.

EXAMPLE 1

Isolation of Plant Mismatch Repair Genes

The ability to increase the hypermutability of host genomes has many commercial and medical applications. The generation of hypermutable plants such as those used in agriculture for livestock feed and human consumption are just one example of many types of applications that can be generated by creating hypermutable organisms. For instance, the creation of crops that are less susceptible to pests or soil pH would greatly increase yield of certain agricultural crops. In addition to greater production of goods, improved crops could increase the ability to grow many generations of crops on the same fields (25-27). Moreover, the ability to affect certain growth traits such as natural pest-resistance, drought-resistance, frost-resistance, increased production, or altered stalk size has many benefits for the production of agricultural products. Recently, it has been demonstrated that genes affecting the biologic activity of the plant growth hormone gibberellin results in crops with shorter stalk length that produce similar amounts of grain yields, however, the fact that the stalks are shorter makes these plants less susceptible to high winds and crop damage (28). The use of hypermutable crops could allow for the selection of shorter plants across many species such as corn, rice, etc, without having to first identify a gene to alter its activity. Another application of hypermutable agricultural products is the generation of crops with enhanced levels of vitamins and nutrients. One can select for enhanced vitamin production in seedlings of MMR defective plants. Recently, it has been demonstrated that altering a gene(s) within a vitamin biosynthetic pathway can result in the production of elevated levels of vitamin E (27,29).

Applications of hypermutable plants include use as crops for agricultural production, increased medicinal entities within plant extracts, chemicals and resins for industrial use, and their use as detoxifying organisms for environmental applications as described (25,26,29).

MutS and mutL homologs can be isolated from plant species libraries using degenerate RT-PCR, and standard Southern hybridization techniques as previously described (3,23, 30). These may serve as reagents for producing MMR defective plant hosts. This process employs methods known by those skilled in the art of gene cloning.

One such approach is the use of degenerate PCR to clone MutS homologs following the methods used by Leach et. al. to clone the human MSH2 (3). Additional degenerate oligonucleotides can be generated and used against conserved domains of bacterial, yeast, and human MutS homologs. Various plant species cDNAs (obtainable from various commercial sources) can be amplified for MutS gene homologs by polymerase chain reaction (PCR). Products are cloned into T-tailed vectors (In Vitrogen) and analyzed by restriction endonuclease digestion. Clones with expected DNA fragment inserts are sequenced using M13 forward and reverse primers located on the vector backbone flanking the cloning site. Fragments containing MMR gene homologs are then used as probes to screen commercially available cDNA libraries from the appropriate species. cDNA contigs are generated to create a cDNA containing the sequence information for the full length MMR gene and its encoded polypeptide. One such example of cloning a plant MMR gene is provided below.

Figure 1A:
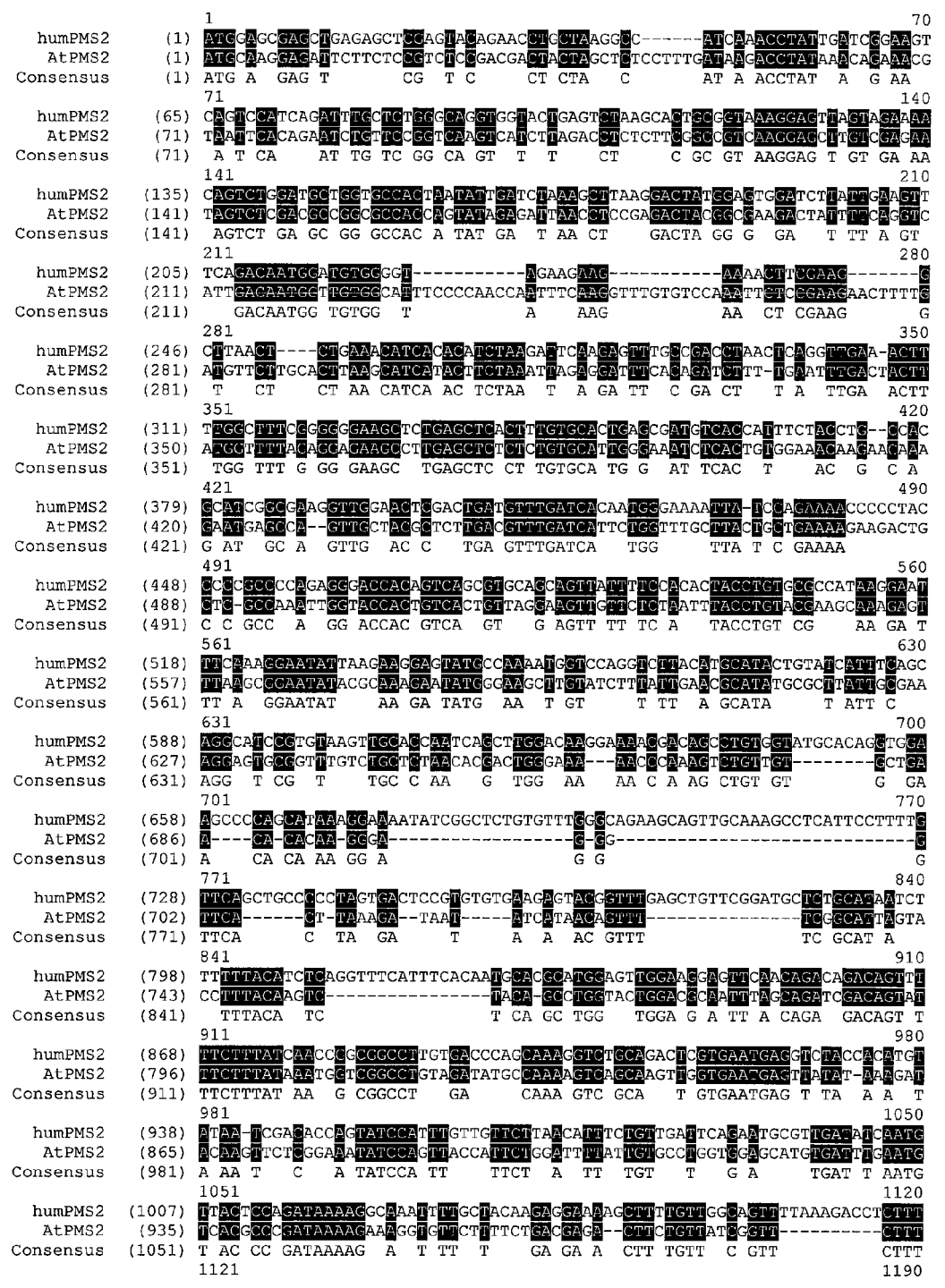
Figure 2:
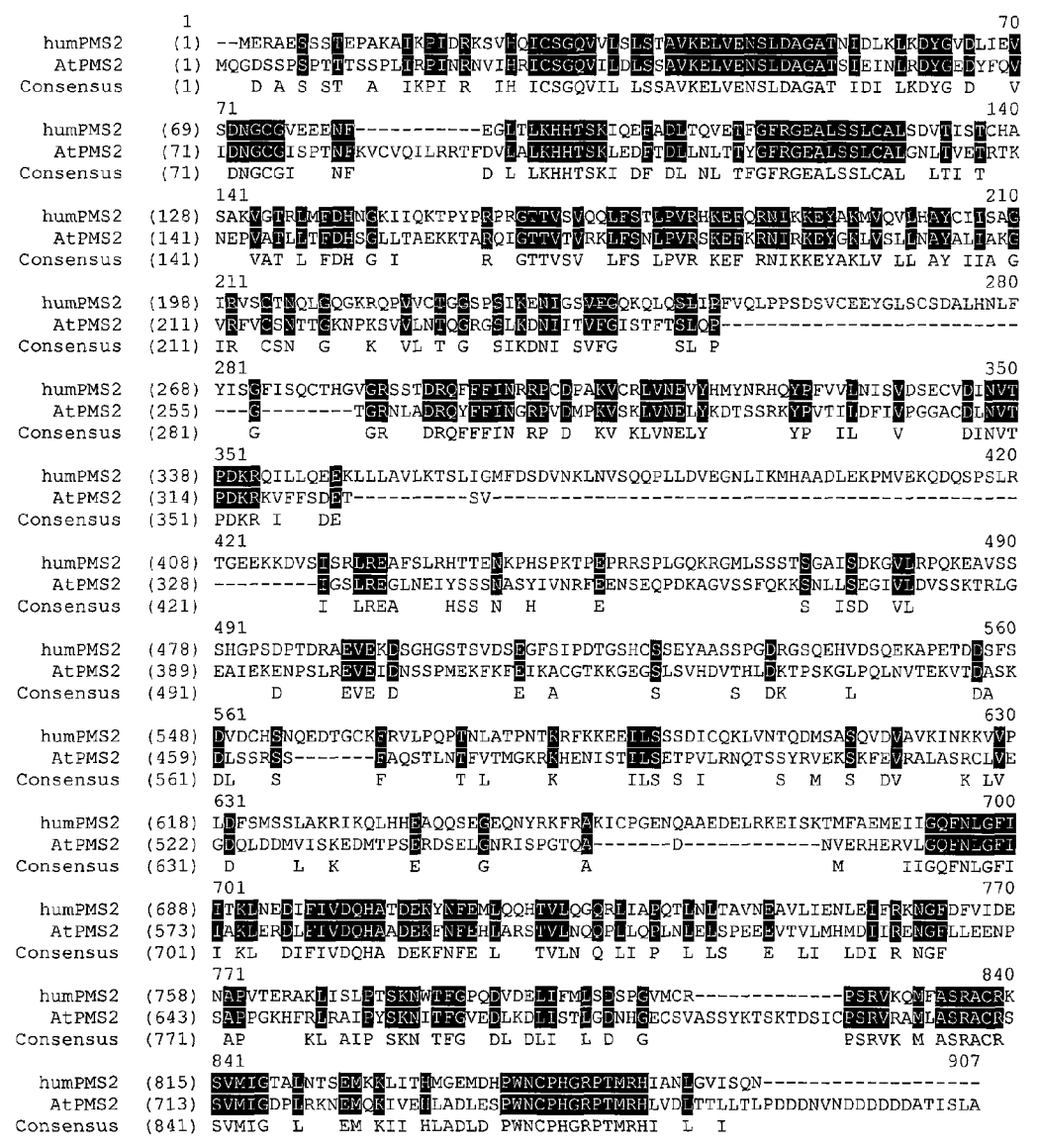

In order to clone mutl homologs, degenerate primers were synthesized to the conserved domains of the mutL gene family by aligning *E. coli*, yeast, mouse, and human mutL genes. These primers are directed to the polynucleotide sequences centered at nt 150 to 350 of the published human PMS2 cDNA (SEQ ID NO: 3). Degenerate PCR was carried out using RNA from *Arabidopsis thaliana* (AT) that was isolated using the RNeasy kit following the manufacturer's protocol (Qiagen). RNAs were reverse transcribed (RT) using SuperscriptfI (Life Technologies) following the manufacturer's protocol. After RT, cDNAs were PCR amplified using degenerate primers in buffers described by Nicolaides et. al. 1995 (23, 30), and reactions were carried out at 95° C. for 30 sec for 1 cycle followed by 94° C. for 30 sec, 45° C. for 60 sec, and 72° C. for 60 sec for 20 cycles. PCR reactions were then diluted 1:10 in water and reamplified using the same primers and buffers. The secondary PCR reactions were carried out at 95° C. for 30 sec for 1 cycle followed by 94° C. for 30 sec, 52° C. for 90 sec, and 72° C. for 90 sec for 35 cycles. Reactions were analyzed by agarose gel electrophoresis. Products of the expected molecular weight were excised and cloned into T-tailed vectors (InVitrogen). Recombinant clones were sequenced and blasted against the public databases. The homolog was found to have homology to the mutL family of genes. Blast search analysis of GenBank found this gene to be part of a "putative" mismatch repair gene identified from the *Arabidopsis* genome project that has never been reported to be transcribed or capable of producing a message. In order to clone the full length, an *Arabidopsis* cDNA library was screened by PCR as well as cDNA from AT plants using 5' primers corresponding to the initiation codon (SEQ ID NO: 1:5'-atg caa gga gat tct tc-3') and the termination codon (SEQ ID NO: 2:5'-tca tgc caa tga gat ggt tgc-3') using buffers and conditions listed above. Amplifications were carried out at 95° C. for 30 sec for 1 cycle followed by 94° C. for 30 sec, 58° C. for 2 min, and 72° C. for 3 min for 35 cycles. Products were analyzed by gel electrophoresis. Products of the expected molecular weights were subcloned into T-tail vectors and sequenced using primers from the cloning vector or using internal primers. FIG. 1 shows the alignment of one *Arabidopsis* homolog, referred to as ATPMS2 (SEQ ID NO: 4), to the human PMS2 cDNA (SEQ ID NO:3) (FIG. 1) and the hPMS2 protein (FIG. 2; SEQ ID NO:11). This gene was found to be homologous (48% identity) to the human PMS2 (SEQ ID NO:3) cDNA and its encoded polypeptide (31% identity) (FIG. 2). Other homologs to the ATPMS2 were also identified from blast searching sequence databases. One mutL homolog is closely related to the MLH1 mammalian homolog and is referred to as ATMLH1 (shown in FIG. 3) and another is closely related to the mammalian PMS1 polypeptide referred to as ATPMS1 (shown in FIG. 4). A phylogenetic tree is shown in FIG. 5 showing the homology of the mutL homologs to the human PMS2 gene.

Degenerate primers can be used for isolating MMR genes from other plant species in a similar fashion.

EXAMPLE 2

Generation of Dominant Negative Alleles of Plant Mismatch Repair Genes

Figure 8:
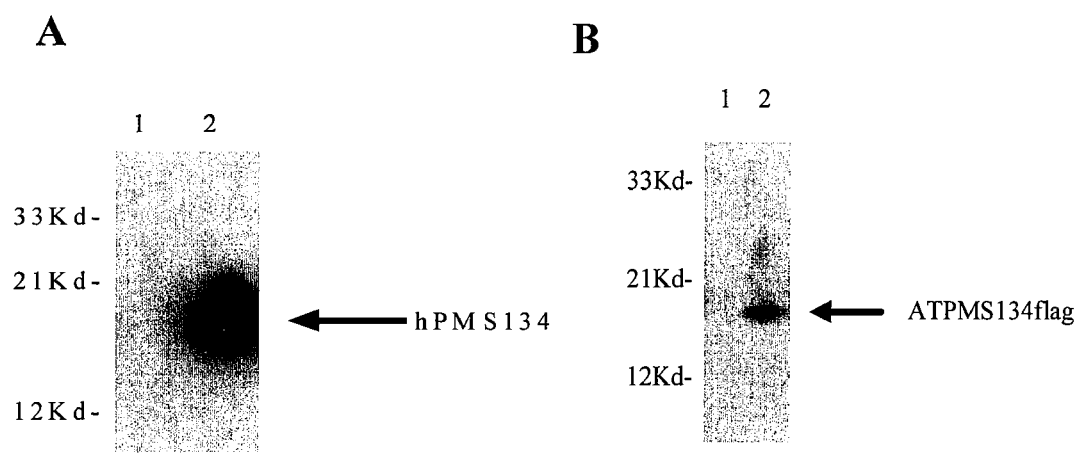
FIGS. 8 A and B. Western blot analysis of bacteria expressing the hPMS134 (FIG. 8A) or the *Arabidopsis thaliana* PMS134 (FIG. 8B) polypeptides.

To demonstrate that putative plant MMR proteins are truly involved in MMR biochemical process, cDNAs are cloned into constitutive (31,32) or inducible (33) bacterial expression vectors for functional studies. Various deletion mutants are generated to produce dominant negative MMR genes. Dominant negative alleles that are identified in the bacterial system are then useful for plant studies. Dominant negative MMR genes are prepared by over-expression of full-length MMR genes or by deletion analysis using standard protocols used by those skilled in the art of molecular biology. One such dominant MMR gene mutant was created by generating a construct with similar domains to that of the human dominant negative PMS2 gene (referred to as PMS134) (13, U.S. Pat. No. 6,146,894). To generate this vector, the ATPMS2 (SEQ ID NO: 4) and hPMS2 cDNA (SEQ ID NO: 3) sequences were aligned and the conserved domain was isolated. FIG. 6 shows a sequence alignment between the human and AT PMS134 cDNAs where a 52% identity is found between the two sequences. At the protein level these domains have a 51% identity (FIG. 7). Dominant negative hPMS134 and ATPMS134 genes were made by PCR and subcloned into bacterial expression vectors. The ATPMS134 was generated by PCR from the cloned cDNA using a sense primer (SEQ ID NO:1) corresponding to the N-terminus and an antisense primer (SEQ ID NO:15) 5' gtcgacttatcacttgtcatcgtcgtc-cttgtagtcgag-cgtagc-aactggctc-3' centered at nt 434 of the ATPMS2 cDNA (SEQ ID NO:4). This primer also contains a flag epitope that will allow protein detection followed by two termination codons. PCR products of the expected molecular weight were gel purified and cloned into T-tail vectors. Recombinant clones were sequenced to ensure authentic sequences. Inserts were then cloned into the inducible pTAC expression vector, which also contains the Ampicillin resistance gene as a selectable marker. The human PMS134 allele was also cloned into the pTAC expression vector as a positive control. Electrocompetent DH5alpha and DH10b bacterial cells (Life Technologies) were electroporated with empty vector, and the loaded vectors pTACATPMS134 and pTAChPMS134, using an electroporator (BioRAd) following the manufacturer's protocol. Bacterial cultures were then plated on to LB agar plates containing 100 µg/ml ampicillin and grown at 37° C. for 14 hours. Ten recombinant clones were then isolated and grown in 5 mls of LB broth containing 50 µg/ml ampicillin plus 50 µM IPTG for 18 hr at 37° C. One hundred microliters were then collected, spun down, and directly lysed in 2×SDS buffer for western blot analysis. For western analysis, equal number of cells were lysed directly in 2×SDS buffer (60 mM Tris, pH 6.8, 2% SDS, 10% glycerol, 0.1 M 2-mercaptoethanol, 0.001% bromophenol blue) and boiled for 5 minutes. Lysate proteins are separated by electrophoresis on 4-12% NuPAGE gels (Novex). Gels are electroblotted onto Immobilon-P (Millipore) in 48 mM Tris base, 40 mM glycine, 0.0375% SDS, 20% methanol and blocked overnight at 4° C. in Tris-buffered saline plus 0.05% Tween-20 and 5% condensed milk. Filters are probed with a polyclonal antibody generated against MMR polypeptide sequence or a fused tag (e.g. FLAG, HIS, etc.) and a horseradish peroxidase conjugated secondary antibody, using chemiluminescence for detection (Pierce). FIG. 8 shows a western blot of a clone that expresses the human PMS134 protein (FIG. 8A, lane 2) using a human PMS2-specific antibody (directed to residues 2-20) of the hPMS134 sequence (see FIG. 1, and SEQ ID NO:6) or the *Arabidopsis* PMS134 protein (FIG. 8B, lane 2) using an anti-FLAG antibody directed to the fusion residues at the C-terminus of the protein. Cells expressing empty vector had no detectable expression.

Figure 9:
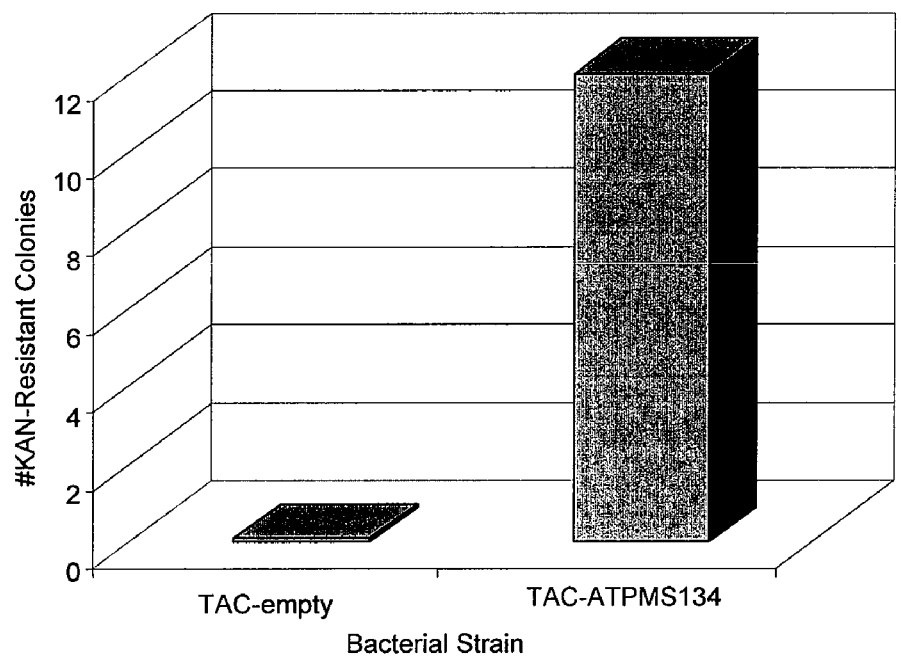
FIG. 9. Expression of plant dominant negative MMR genes produces hypermutability in bacteria, demonstrating the functionality of plant MMR proteins. Briefly, bacteria containing the empty vector of the TAC ATPMS134 expression vector were grown and plated on kanamycin-containing Lbagar plates. The host bacteria are susceptible to KAN bactericidal activity. Bacterial cultures expressing the hPMS134 gene resulted in genetic alteration of the bacterial host and the generation of clones that are KAN resistant.

Bacterial clones expressing the hPMS134, ATPMS134 or the empty vector were grown in liquid culture for 24 hr at 37° C. in the presence of 50 µg/ml ampicillin plus 50 µM IPTG. The next day, cultures were diluted 1:10 in medium containing 50 µM IPTG plus ampicillin or ampicillin plus 25 µg/ml kanamycin (AK) and cultures were grown for 18 hr at 37° C. The following day, a 0.1 µl aliquot (2 µl diluted in 1000 µl of LB medium and used 50 µl for plating) of cells grown in Amp medium were plated on LB-agar plates containing 40 µg/ml of 5-bromo-4-chloro-3-indolyl-B-D-galactoside (X-gal) plus 100 µg/ml ampicillin (AMP), while a 1 µl aliquot (1 µl diluted in 100 µl of LB medium and used 100 µl for plating) of cells grown in AK medium were plated on LB-agar plates containing X-gal and 50 µg/ml kanamycin (KAN). Plates were incubated for 18 hours at 37° C. The results from these studies show that cells expressing the hPMS134 or the ATPMS134 polypeptides displayed increased mutation rates in the genome of the DH10B bacterial strain which resulted in the production of KAN resistant clones (FIG. 9). Following the mutagenesis protocol described above, bacterial cells expressing the plant ATPMS134 were found to have an increase in the number of KAN resistant cells (12 clones) in contrast to cells expressing the empty vector, which yielded no KAN resistant clone. These data demonstrate that dominant negative ATPMS134 MMR genes are useful for creating hypermutable organisms that can generate phenotypically diverse offspring when put under selective conditions. Moreover, these data demonstrate that plants also use the conserved MMR process for genomic stability.

Dominant negative plant MMR gene mutants are also analyzed using mammalian cell systems. In this case, plant MMR gene cDNAs are cloned into eukaryotic expression vectors as described (13,34) and cells expressing dominant negative mutants are analyzed by measuring stability of endogenous microsatellite markers and biochemical activity of cell extracts from lines expressing dominant negative MMR gene alleles. Such methods are known by those skilled in the art and previously described (13).

EXAMPLE 3

Inhibition of Plant MMR Activity by Dominant Negative MMR Alleles Produces Genetic Hypermutability and Microsatellite Instability Dominant negative alleles of human and AT MMR genes identified using bacterial and or mammalian systems can be used for plants. To test the hypothesis that dominant negative MMR gene alleles produce global hypermutability in plants, the hPMS134 and ATPMS134 cDNAs were expressed in plants. These alleles have been found to work across species where the introduction of these genes into MMR proficient bacterial or mammalian cells renders the cells MMR deficient. Assays to carry out these studies are described below. Engineering Plant Expression Vectors to Express the PMS134 Dominant Negative Alleles.

Figure 10:
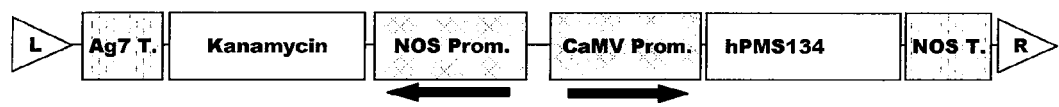
FIG. 10. Schematic diagram of a plant dominant-negative MMR expression vector. Ag7 T. and NOS T.=gene 7 and Nopaline Synthase poly(A) signals, respectively. NOS Prom and CaMV Prom=Nopaline Synthase and Cauliflower Mosaic Virus promoters, respectively. L and R=left and right T=DNA border repeats, respectively. Arrows indicate direction of transcription.

A BamH I fragment containing the hPMS134 cDNA was obtained from the pSG5PMS134 plasmid (ref 13) and cloned into the corresponding sites of the pEF1SP1-V5 vector (InVitrogen). The resulting vector (pEF-PMS134-sense) was then digested with Pme I to release a blunted DNA fragment containing the PMS134 cDNA. This fragment was then subcloned into the blunt Sma I and EcoICR I sites of the pGPTV-KAN binary plant expression vector (American Type Culture Collection). One clone, named pCMV-hPMS134-Kan (see FIG. 10), was sequenced to confirm that the vector contained authentic promoter and gene insert sequences. A schematic diagram of the pCMV-hPMS134-Kan vector is shown in FIG. 10.

Generation of hPMS134-Expressing *Arabidopsis Thaliana* Transgenic Plants.

*Agrobacterium tumefaciens* cells (agrobacteria) are used to shuttle genes into plants. To generate PMS134-expressing *Arabidopsis thaliana* (*A. thaliana*) plants, *Agrobacterium tumefaciens* cells (strain GV3101) were electroporated with pCMV-hPMS134-Kan or the pBI-121 (BRL) control binary vector. The pBI-121 control contains the CaMV promoter driving the expression of the .beta.-glucuronidase cDNA (GUS) and serves as a control. Both vectors carry the neomycin phosphotransferase (NPTII) gene that allows selection of agrobacteria and plants that contain the expression vector. One-month old *A. thaliana* (ecotype Columbia) plants were infected by immersion in a solution containing 5% sucrose, 0.05% silwet, and binary vector-transformed agrobacteria cells for 10 seconds. These plants were then grown at 25° C.

under a 16 hour day and 8 hour dark photoperiod. After 4 weeks, seeds (referred to as T1) were harvested and dried for 5 days at 4° C. Thirty thousands seeds from ten CMV-hPMS134-Kan-transformed plants and five thousand seeds from two pBI-121-transformed plants were sown in solid Murashige and Skoog (MS) media plates in the presence of 50 µg/ml of kanamycin (KAN). Three hundred plants were found to be KAN resistant and represented PMS134 expressing plants. These plants along with 300 control plants were grown in MS media for two weeks and then transferred to soil. Plants were grown for an additional four weeks under standard conditions at which time T2 seeds were harvested.

To confirm the integration and stability of the PMS134 gene in the plant genome, gene segregation and PCR analyses were conducted. Commonly, three out of four T1 plants transformed by agrobacteria technology are expected to carry the vector inserted within a single locus and are therefore considered heterozygous for the integrated gene. Approximately 75% of the seeds (T2) generated from most of the T1 plants were found KAN-resistant and this in accordance with the expected 1:2:1 ratio of null (no hPMS134 containing plants), heterozygous, and homozygous plants, respectively, in self-pollinating conditions. To confirm that these plants contained the hPMS134 expression vector, genomic DNA was isolated from leaves of T1 plants using the DNAzol-mediated technique following the manufacturer's suggestion (BRL-Life Technologies). One nanogram of genomic DNA was analyzed by polymerase chain reaction (PCR) to confirm the presence of the hPMS134 gene. PCR was carried out for 25 cycles with the following parameters: 95° C. for 30 seconds; 55° C. for 1 minute; and 72° C. for 2 minutes using hPMS134-specific sense (SEQ ID NO: 7: 5'-tct aga cat gga gcg agc tga gag ctc-3') and antisense (SEQ ID NO: 8:5'-tct aga agt tcc aac ctt cgc cga tgc-3') primers. Positive reactions were observed in DNA from pCMV-hPMS134-Kan-transformed plants and not from pBI-121-transformed plants, thus confirming the integration of this vector.

Figure 11:
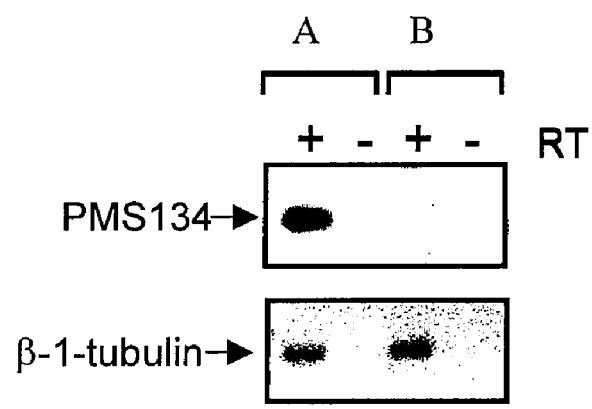
FIG. 11. Transgenic plants containing the PMS134-KAN vector express the dominant negative hPMS134 gene. Message analysis for T1 plants shows steady state expression of dominant negative MMR genes in PMS134-Kan plants (A lanes) while non is observed in control plants (B lanes). Tubulin was used as an internal control to monitor sample loading and integrity.

In order to assess the expression of hPMS134 in T1 plants, leaf tissue was collected from T1 plants, homogenized in liquid nitrogen using glass pestles, and suspended in RLT lysing buffer (Qiagen, RNeasy plant RNA extraction kit). Five micrograms of total RNA was purified according to the manufacturer's suggested protocol and then loaded onto a 1.2% agarose gel (1.times. MOPS buffer, 3% formaldehyde), size-fractionated by electrophoresis, and transferred onto N-Hybond+ membrane (Amersham). Each membrane was incubated at 55° C. in 10 ml of hybridization solution (North2South labeling kit, Pierce) containing 100 ng of PMS134, tubulin, or KAN cDNA probes, which were generated by PCR amplification, according to the manufacturer's directions. Membranes were washed three times in 2.times.SSC, 0.1% SDS at 55° C., and three times in 2.times.SSC at ambient temperature. Detection was carried out using enhanced chemiluminescence (ECL). Expression was also carried out by reverse trascriptase PCR as described above using polyA isolated mRNA that was isolated over a oligo dT column (Qiagen). A representative example of these studies are shown in FIG. 11. Here hPMS134 expression was detected in three out of ten analyzed pCMV-hPMS134-Kan transgenic lines, while no signal was found in the ten pBI-121 transformed plants analyzed. Immunoblot using whole lysates is used to confirm protein expression. Collectively these studies demonstrate the generation of hPMS134 expressing transgenic *A. thaliana* plants.

Molecular Characterization of PMS134-Expressing Plants

Figure 12:
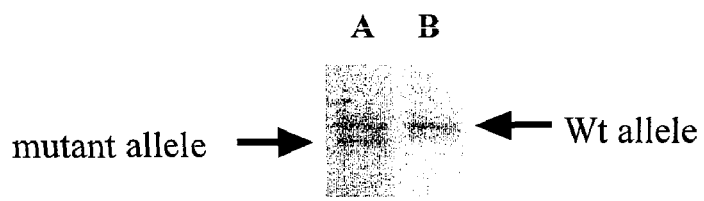
FIG. 12. Microsatellite instability in plants expressing dominant negative MMR hPMS134 gene.

MMR is a process that is involved in correcting point mutations and "slippage" mutations within repetitive mono-, di-, and tri-nucleotide (microsatellite) repeats that occur throughout the genome of an organism after cellular replication. This process is very similar to a computer spell check function. The inactivation of MMR has been shown to result in global genomic hypermutation whereby cells with defective MMR experience over a one thousand-fold increase in point mutations and microsatellite instability (MI) (mutations within repetitive sequences) throughout their genomes per division. (35). MMR deficiency is the only known process capable of producing MI and has been used as a marker to detect cells with MMR dysfunction (36). Microsatellites serve as molecular tools to measure the inactivation of MMR that occurs by the defective MMR due to but not limited to expression of dominant negative MMR genes, double stranded RNA interference vectors, or inhibition by antisense nucleotides, or by gene knockout. In *A. thaliana*, a series of poly-A (A)n, (CA)n and (GA)n sequences were identified from genome searches using EMBL and GenBank databases. To demonstrate that hPMS134 expression could produce MI in *A. thaliana*, we analyzed microsatellites in T1 plants by PCR analyses. Initially we monitored three microsatellites, ATHACS, Nga280, and Nga128 with published primers that have been previously used to map the *Arabidopsis* genome (37). Briefly, DNA was extracted from *A. thaliana* leaves as described above. 10 ngs of plant genomic DNA was used as template for PCR amplification using the following amplification conditions: 94° C. for 15 sec, 55° C. for 15 sec and 72° C. for 30 seconds. PCR products were analyzed on 5% Metaphor agarose (BioWhittaker Molecular Applications) and ethidium bromide staining. In one transgenic pCMV-PMS134-Kan line, we detected a double product, likely representing a new allele of the polymorphic nga280 locus (FIG. 12). These data demonstrate the ability to produce MMR deficiency and MI in plants expressing the hPMS134 dominant negative allele and provide a molecular tool for screening MMR-defective plants.

Biochemical assays for mismatch repair. MMR activity in nuclear extracts is performed as described, using 24 finol of substrate as described (13). Complementation assays are done by adding .about.100 ng of purified MutL or MutS components to 100 µg of nuclear extract, adjusting the final KCl concentration to 100 mM. The substrates used in these experiments will contain a strand break 181 nucleotides 5' or 125 nucleotides 3' to the mismatch.

EXAMPLE 4

Inactivation of MMR Leads to Plants with New Phenotypes

Figure 13:
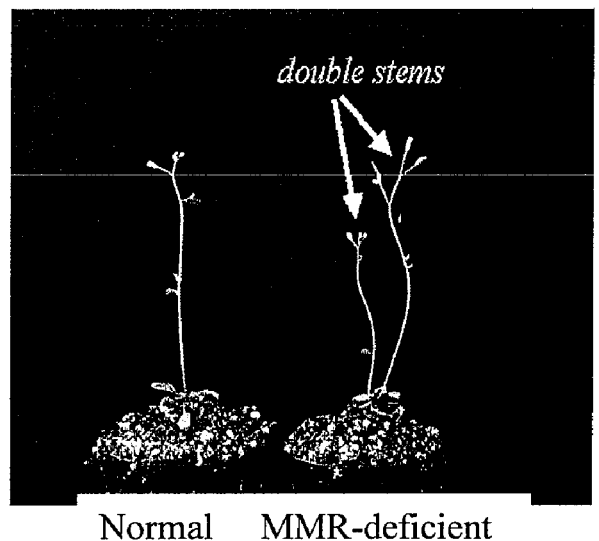
FIG. 13. MMR defective plants produce new phenotypes. Plants with decreased MMR produce offspring with two shoot apical meristems (SAM) in contrast to control plants exhibiting a single SAM. Seeds from the MMR defective plant have been obtained and offspring have the same "double-meristem" trait.

We demonstrated the ability of the defective MMR to produce molecular changes within plants. The objective of this section is to demonstrate the ability to generate MMR defective plants with macroscopic output traits. One way to measure for plants with new phenotypes is to grow plants under toxic conditions, such as but not limited to high levels of toxic ions, pest-infection, drought conditions, or extreme temperatures to identify a minority of plants with new output traits, i.e., resistance. Another way to score for plants with new phenotypes is through physical differences of MMR defective plants grown in standard conditions. An example of MMR-defective plants with new phenotypes include the generation of plants with double shoot apical meristems (FIG. 13) as well as plants with altered chlorophyll production rendering plants albino (data not shown). In FIG. 13, we show a typical wild type plant (left, labeled normal) and a plant produced from the MMR defective group (right, labeled MMR deficient). The double-meristem trait was not observed in greater than 500 normal plants. The double-meristem trait does not appear to be due to transgene integration since segregation analysis reveals the ability to generate double-meristem plants in the absence of transgene positive plants while MMR proficient control plants with other transgene vectors (pBI-121) did not produce this phenotype (data not shown). These data suggest that defective MMR produced a mutation or mutations within the plant genome that altered the normal biochemical function of the host to produce a new output trait.

These data demonstrate the ability to create plant subtypes with new genetic and phenotypic traits by blocking the endogenous MMR process of the plant cell or whole organism.

EXAMPLE 5

Inhibition of Plant MMR Activity Using Molecular Approaches

This application teaches of the use of inhibiting MMR activity in a plant to produce genetically altered offspring with new phenotypes.

The inhibition of MMR activity in a host organism can be achieved by introducing a dominant negative allele as shown in FIGS. 11 and 12. Other ways to suppress MMR activity of a host is by: knocking out alleles of a MMR protein through homologous recombination (38); blocking MMR protein dimerization with other subunits (which is required for activity) by the introduction of polypeptides into the host via transfection methods; knocking out the expression of a MMR gene using anti-sense oligonucleotides (20), and/or the use of double stranded RNA interference genes (21).

MMR Gene Knockouts.

Data shown in EXAMPLE 1 demonstrate that plants contain MMR gene homologs that can be genetically engineered to produce altered biochemical activities. Data presented in EXAMPLES 3 and 4 demonstrate that defective MMR in plants can produce hypermutable parental plants and offspring. Together, these data demonstrate that inhibiting endogenous MMR genes by targeting vectors of the particular MMR gene can lead to hypermutability of a plant host that generate offspring with altered genetic loci and/or new phenotypes as described in EXAMPLES 3, 4, and 5. Hypermutable seedlings can also be produced with "knocked out" MMR genes using methods known by those skilled in the art. These can be used to produce genetically diverse offspring for commercial and medical applications (38). Cells will be confirmed to have lost the expression of the MMR gene using standard northern techniques and determined to be MMR defective using microsatellite analysis as described in EXAMPLE 3.

Blocking Polypeptides.

MMR subunits (MutS and MutL proteins) interact to form active MMR complexes. Peptides are able to specifically inhibit the binding of two proteins by competitive inhibition. Isolation of plant MMR genes allows for the elucidation of primary amino acid structures as described in EXAMPLE 1. Peptides containing some but not all of the domains can be synthesized from domains of the particular MMR gene and introduced into host plants using methods known by those skilled in the art (22). Like truncated PMS134, such peptides will compete with functional full length proteins for binding and form enzymatically inactive MMR complexes. The data indicate that the domains which are C-terminal to the 134 position in human PMS2 are dispensible for binding and necessary for enzymatic activity. As shown herein, a similar domain structure is also found in plant PMS2. Seedlings exhibiting hypermutability will be useful to produce genetically diverse offspring for commercial and medical applications.

RNA Blockade and Double Stranded Interference.

MMR subunits (MutS and MutL proteins) interact to form active MMR complexes. Peptides are able to specifically inhibit the binding of two proteins by competitive inhibition. Antisense oligonucleotides are synthesized against the cDNA sequence of plant MMR homologs identified in EXAMPLE 1 (20). Antisense molecules are then introduced into host plants using methods described in EXAMPLE 2 or through the bathing of seedlings or plantlets. Seedlings exhibiting hypermutability will be useful to produce genetically diverse offspring for commercial and medical applications.

Double stranded interference vectors are also useful for blocking expression/function of a plant MMR gene. The plant gene is expressed in both sense and antisense orientations from a transfection vector and the endogenous gene expression is suppressed by endogenous silencing processes (21).

Discussion

Plants contain MMR genes that code for MMR functional proteins. Expression of dominant negative plant MMR proteins results in an increase in microsatellite instability and hypermutability in plants. This activity is due to the inhibition of MMR biochemical activity in these hosts. The data provided within this application demonstrates the blockade of MMR in a plant to produce genetic changes that lead to the production of offspring or cells with new output traits. This method is applicable to generate crop plants with new output traits as well as plant cells exhibiting new biochemicals for commercial use.

REFERENCES CITED

Each of which is Expressly Incorporated Herein for all Purposes

1. Liu, B., Parsons, R., Papadopoulos, N., Nicolaides, N. C., Lynch, H. T., Watson, P., Jass, J. R., Dunlop, M., Wyllie, A., Peltomaki, P., de la Chapelle, A., Hamilton, S. R., Vogelstein, B., and Kinzler, K. W. 1996. Analysis of mismatch repair genes in hereditary non-polyposis colorectal cancer patients. Nat. Med. 2:169-174.
2. Bronner, C. E., Baker, S. M., Morrison, P. T., Warren, G., Smith, L. G., Lescoe, M. K., Kane, M., Earabino, C., Lipford, J., Lindblom, A., Tannergard, P., Bollag, R. J., Godwin, A., R., Ward, D. C., Nordenskjold, M., Fishel, R., Kolodner, R., and Liskay, R. M. 1994. Mutation in the DNA mismatch repair gene homologue hMLH1 is associated with hereditary non-polyposis colon cancer. Nature 368:258-261.
3. Leach, F. S., Nicolaides, N. C, Papadopoulos, N., Liu, B., Jen, J., Parsons, R., Peltomaki, P., Sistonen, P., Aaltonen, L. A., Nystrom-Lahti, M., Guan, X. Y., Zhang, J., Meltzer, P. S., Yu, J. W., Kao, F. T., Chen, D. J., Cerosaletti, K. M., Fournier, R. E. K., Todd, S., Lewis, T., Leach R. J., Naylor, S. L., Weissenbach, J., Mecklin, J. P., Jarvinen, J. A., Petersen, G. M., Hamilton, S. R., Green, J., Jass, J., Watson, P., Lynch, H. T., Trent, J. M., de la Chapelle, A., Kinzler, K. W., and Vogelstein, B. 1993. Mutations of a mutS homolog in hereditary non-polyposis colorectal cancer. Cell 75:1215-1225.
4. Nicolaides, N. C., Papadopoulos, N., Liu, B., Wei, Y. F., Carter, K. C., Ruben, S. M., Rosen, C. A., Haseltine, W. A., Fleischmann, R. D., Fraser, C. M., Adams, M. D., Venter, C. J., Dunlop, M. G., Hamilton, S. R., Petersen, G. M., de la Chapelle, A., Vogelstein, B., and kinzler, K. W. 1994. Mutations of two PMS homologs in hereditary nonpolyposis colon cancer. Nature 371: 75-80.
5. Nicolaides, N. C., Palombo, F., Kinzler, K. W., Vogelstein, B., and Jiricny, J. 1996. Molecular cloning of the N-terminus of GTBP. Genomics 31:395-397.
6. Palombo, F., Gallinari, P., Iaccarino, I., Lettieri, T., Hughes, M. A., Truong, O., Hsuan, J. J., and Jiricny, J. 1995. GTBP, a 160-kilodalton protein essential for mismatch-binding activity in human cells. Science 268:1912-1914.
7. Papadopoulos, N., Nicolaides, N. C., Wei, Y. F., Carter, K. C., Ruben, S. M., Rosen, C. A., Haseltine, W. A., Fleischmann, R. D., Fraser, C. M., Adams, M. D., Venter, C. J., Dunlop, M. G., Hamilton, S. R., Petersen, G. M., de la Chapelle, A., Vogelstein, B., and kinzler, K. W. 1994. Mutation of a mutL homolog is associated with hereditary colon cancer. Science 263:1625-1629.
8. Perucho, M. 1996. Cancer of the microsattelite mutator phenotype. Biol. Chem. 377:675-684.
9. Strand, M., Prolla, T. A., Liskay, R. M., and Petes, T. D. Destabilization of tracts of simple repetitive DNA in yeast by mutations affecting DNA mismatch repair. 1993. Nature 365:274-276.
10. Ma A H, Xia L, Littman S J, Swinler S, Lader G, Polinkovsky A, Olechnowicz J, Kasturi L, Lutterbaugh J, Modrich P, Veigl M L, Markowitz S D, Sedwick W D. 2000. Somatic mutation of hPMS2 as a possible cause of sporadic human colon cancer with microsatellite instability. Oncogene 19:2249-2256.
11. Parsons, R., Li, G. M., Longley, M. J., Fang, W. H., Papadopolous, N., Jen, J., de la Chapelle, A., Kinzler, K. W., Vogelstein, B., and Modrich, P. 1993. Hypermutability and mismatch repair deficiency in RER+ tumor cells. Cell 75:1227-1236.
12. Li, G.-M., and Modrich, P. 1995. Restoration of mismatch repair to nuclear extracts of H6 colorectal tumor cells by a heterodimer of human mutL homologs. Proc. Natl. Acad. Sci. USA 92:1950-1954.
13. Nicolaides N. C. et. al. 1998. A naturally occurring hPMS2 mutation can confer a dominant negative mutator phenotype. Mol Cell Biol. 18:1635-1641.
14. Modrich, P. 1994. Mismatch repair, genetic stability, and cancer. Science 266:1959-1960.
15. Pang, Q., Prolla, T. A., and Liskay, R. M. 1997. Functional domains of the *Saccharomyces cerevisiae* Mlh1p and Pms1p DNA mismatch repair proteins and their relevance to human hereditary nonpolyposis colorectal cancer-associated mutations. Mol. Cell. Biol. 17:4465-4473.
16. Harfe, B. D., and Jinks-Robertson, S. 2000. DNA MISMATCH REPAIR AND GENETIC INSTABILITY. Annu Rev Genet 34:359-399.
17. Culligan, K. M, and Hays, J. B. 1997. DNA mismatch repair in plants. An *Arabidopsis thaliana* gene that predicts a protein belonging to the MSH2 subfamily of eucaryotic MutS homologs. Plant Physiol. 115:833-839.
18. Jean M, Pelletier J, Hilpert M, Belzile F, and Kunze R. 1999. mutl Plant Isolation and characterization of AtMLH1, a MutL homologue from *Arabidopsis thaliana*. Mol Gen Genet. 262:633-642.
19. de Wind N., Dekker, M., Berns, A., Radman, M., and Riele, H. T. 1995. Inactivation of the mouse Msh2 gene results in mismatch repair deficiency, methylation tolerance, hyperrecombination, and predisposition to cancer. Cell 82:321-300.
20. Hackett R M, Ho C W, Lin Z, Foote H C, Fray R G, Grierson D. 2000. Antisense inhibition of the Nr gene restores normal ripening to the tomato never-ripe mutant, consistent with the ethylene receptor-inhibition model. Plant Physiol 124:1079-1086.
21. Chuang C F, Meyerowitz E M. 2000. Specific and heritable genetic interference by double-stranded RNA in *Arabidopsis thaliana*. Proc Natl Acad Sci USA 97:4985-4990.
22. Takeuchi M, Ueda T, Sato K, Abe H, Nagata T, and Nakano A. 2000. A dominant negative mutant of sari GTPase inhibits protein transport from the endoplasmic reticulum to the golgi apparatus in tobacco and *arabidopsis* cultured cells. Plant J. 23:517-525.
23. Nicolaides, N. C., Carter, K. C., Shell, B. K., Papadopoulos, N., Vogelstein, B., and Kinzler, K. W. 1995. Genomic organization of the human PMS2 gene family. Genomics 30:195-206.
24. Horii, A., et. al. 1994. Cloning, characterization and chromosomal assignment of the human genes homologous to yeast PMS1, a member of mismatch repair genes. Biochem Biophys Res Commun. 204:1257-1264.
25. Moffat, A. S., 1999. Engineering plants to cope with metals. Science 285:369-370.
26. Mazur, B., Krebbers, E., and Tingey, S. 1999. Gene discovery and product development for grain quality traits. Science. 285:372-375.
27. Shintani, D., and DellaPenna, D. 1998. Elevating the Vitamin E content of plants through metabolic engineering. Science. 282:2098-2100.
28. Peng, J., Richards, D. E., Hartley, N. M., Murphy, G. P., et. al. 1999. "Green revolution" genes encode for mutant gibberellin response modulators. Nature. 256-261.
29. DellaPenna, D. 1999. Nutritional genomics: Manipulating plant micronutrients to improve human health. Science. 285:375-379.
30. Nicolaides N. C., Kinzler, K. W., and Vogelstein, B. 1995. Analysis of the 5' region of PMS2 reveals heterogenous transcripts and a novel overlapping gene. Genomics 29:329-334.
31. Murai, N., Sutton, D. W., Murray, M. G., Slightom, J. L., Merlo, D. J., et. al. 1983. Science. 222:476-???.
32. Koziel, M. G., Adams, T. L., Hazlet, M. A., et. al., 1984. J. MOL. Appl. Genet. 2:549-560.
33. Kaulen, H., Schell, J., and Kreuzaler, F. 1986. EMBO J. 5:1
34. Nicolaides, N. C., Correa, I., Casadevall, C., Travali, S., Soprano, K. J., and Calabretta, B. 1992. The Jun family members, c-JUN and JUND, transactivate the human c-myb promoter via an Ap1 like element. J. Biol. Chem. 267, 19665-19672.
35. Wheeler J M, Loukola A, Aaltonen L A, Mortensen N J, and Bodmer W F. 2000. The role of hypermethylation of the hMLH1 promoter region in HNPCC versus MSI+ sporadic colorectal cancers. J. Med. Genet. 37:588-592.
36. Hoang J M, Cottu P H, Thuille B, Salmon R J, Thomas G, and Hamelin R. 1997. BAT-26, an indicator of the replication error phenotype in colorectal cancers and cell lines. Cancer Res 57:300-303.
37. Bell, C. J., et. al. Genomics, 19:137-144, 1994.
38. Gal, S., Pisan, B., Hohn, T., Grimsley, N., and Hohn, B. 1991. Genomic homologous recombination in planta. EMBO J. 10:1571-1578.

We claim:

1. A method for generating a mutation in a gene of interest in a plant cell, comprising the steps of:
   growing a hypermutable plant cell comprising the gene of interest and a PMS2-134 allele;
   testing the cell by analyzing a phenotype caused by the gene of interest or by analyzing a protein encoded by the gene of interest to determine whether the gene of interest harbors a mutation.

2. The method of claim 1 wherein the step of testing comprises analyzing a protein encoded by the gene of interest.

3. The method of claim 1 wherein the step of testing comprises analyzing a phenotype caused by the gene of interest.

4. The method of claim 1 wherein the plant cell is made by the process of introducing a polynucleotide comprising a PMS2-134 allele into a plant cell, whereby the cell becomes hypermutable.

5. The method of claim 4 wherein the step of testing comprises analyzing a protein encoded by the gene of interest.

6. The method of claim 4 wherein the step of testing comprises analyzing a phenotype caused by the gene of interest.

7. A method for generating a mutation in a gene of interest in a plant, comprising the steps of:
   growing a plant comprising the gene of interest and a polynucleotide encoding a PMS2-134 allele;
   testing the plant cell by analyzing a phenotype caused by the gene of interest or by analyzing a protein encoded by the gene of interest to determine whether the gene of interest harbors a mutation.

8. The method of claim 7 wherein the step of testing comprises analyzing a protein encoded by the gene of interest.

9. The method of claim 7 wherein the step of testing comprises analyzing a phenotype caused by the gene of interest.

10. The method of claim 7 wherein the plant is made by the process of introducing a polynucleotide comprising a PMS2-134 allele into a plant, whereby the plant becomes hypermutable.

11. The method of claim 10 wherein the step of testing comprises analyzing a protein encoded by the gene of interest.

12. The method of claim 10 wherein the step of testing comprises analyzing the phenotype of the gene of interest.

* * * * *

SEQUENCE LISTING

<160> NUMBER OF SEQ ID NOS: 15

<210> SEQ ID NO 1
<211> LENGTH: 17
<212> TYPE: DNA
<213> ORGANISM: Human sapiens

<400> SEQUENCE: 1
atgcaaggag attcttc                                                        17

<210> SEQ ID NO 2
<211> LENGTH: 21
<212> TYPE: DNA
<213> ORGANISM: Human sapiens

<400> SEQUENCE: 2
tcatgccaat gagatggttg c                                                   21

<210> SEQ ID NO 3
<211> LENGTH: 2589
<212> TYPE: DNA
<213> ORGANISM: Human sapiens

<400> SEQUENCE: 3
atggagcgag ctgagagctc gagtacagaa cctgctaagg ccatcaaacc tattgatcgg           60
aagtcagtcc atcagatttg ctctgggcag gtggtactga gtctaagcac tgcggtaaag          120
gagttagtag aaaacagtct ggatgctggt gccactaata ttgatctaaa gcttaaggac          180
tatggagtgg atcttattga agtttcagac aatggatgtg gggtagaaga agaaaacttc          240
gaaggcttaa ctctgaaaca tcacacatct aagattcaag agtttgccga cctaactcag          300
gttgaaactt ttggctttcg gggggaagct ctgagctcac tttgtgcact gagcgatgtc          360
accatttcta cctgccacgc atcggcgaag gttggaactc gactgatgtt tgatcacaat          420
gggaaaatta tccagaaaac cccctacccc cgcccagag ggaccacagt cagcgtgcag           480
cagttatttt ccacactacc tgtgcgccat aaggaatttc aaaggaatat taagaaggag          540
tatgccaaaa tggtccaggt cttacatgca tactgtatca tttcagcagg catccgtgta          600
agttgcacca atcagcttgg acaaggaaaa cgacagcctg tggtatgcac aggtggaagc          660
cccagcataa aggaaaatat cggctctgtg tttgggcaga agcagttgca aagcctcatt          720
ccttttgttc agctgccccc tagtgactcc gtgtgtgaag agtacggttt gagctgttcg          780
gatgctctgc ataatctttt ttacatctca ggtttcattt cacaatgcac gcatggagtt          840
ggaaggagtt caacagacag acagttttc tttatcaacc ggcggccttg tgacccagca           900
aaggtctgca gactcgtgaa tgaggtctac cacatgtata tcgacaccag tatccatttt          960
gttgttctta acatttctgt tgattcagaa tgcgttgata tcaatgttac tccagataaa         1020
aggcaaattt tgctacaaga ggaaaagctt ttgttggcag ttttaaagac ctctttgata         1080
ggaatgtttg atagtgatgt caacaagcta atgtcagtc agcagccact gctggatgtt          1140
gaaggtaact taataaaaat gcatgcagcg gatttggaaa agcccatggt agaaaagcag         1200
gatcaatccc cttcattaag gactggagaa gaaaaaaaag acgtgtccat tccagactg          1260 cgagaggcct tttctcttcg tcacacaaca gagaacaagc tcacagccc aaagactcca         1320 gaaccaagaa ggagccctct aggacagaaa aggggtatgc tgtcttctag cacttcaggt         1380
gccatctctg acaaaggcgt cctgagacct cagaaagagg cagtgagttc cagtcacgga         1440

-continued

| | |
|---|---|
| cccagtgacc ctacggacag agcggaggtg gagaaggact cggggcacgg cagcacttcc | 1500 |
| gtggattctg aggggttcag catcccagac acgggcagtc actgcagcag cgagtatgcg | 1560 |
| gccagctccc caggggacag gggctcgcag gaacatgtgg actctcagga gaaagcgcct | 1620 |
| gaaactgacg actcttttc agatgtggac tgccattcaa accaggaaga taccggatgt | 1680 |
| aaatttcgag ttttgcctca gccaactaat ctcgcaaccc caaacacaaa gcgttttaaa | 1740 |
| aaagaagaaa ttcttccag ttctgacatt tgtcaaaagt tagtaaatac tcaggacatg | 1800 |
| tcagcctctc aggttgatgt agctgtgaaa attaataaga agttgtgcc cctggacttt | 1860 |
| tctatgagtt ctttagctaa acgaataaag cagttacatc atgaagcaca gcaaagtgaa | 1920 |
| ggggaacaga attacaggaa gtttagggca agatttgtc ctggagaaaa tcaagcagcc | 1980 |
| gaagatgaac taagaaaaga gataagtaaa acgatgtttg cagaaatgga aatcattggt | 2040 |
| cagtttaacc tggatttat aataaccaaa ctgaatgagg atatcttcat agtggaccag | 2100 |
| catgccacgg acgagaagta taacttcgag atgctgcagc agcacaccgt gctccagggg | 2160 |
| cagaggctca tagcacctca gactctcaac ttaactgctg ttaatgaagc tgttctgata | 2220 |
| gaaaatctgg aaatatttag aaagaatggc tttgattttg ttatcgatga aaatgctcca | 2280 |
| gtcactgaaa gggctaaact gatttccttg ccaactagta aaaactggac cttcggaccc | 2340 |
| caggacgtcg atgaactgat cttcatgctg agcgacagcc ctggggtcat gtgccggcct | 2400 |
| tcccgagtca agcagatgtt tgcctccaga gcctgccgga gtcggtgat gattgggact | 2460 |
| gctcttaaca caagcgagat gaagaaactg atcacccaca tggggagat ggaccacccc | 2520 |
| tggaactgtc cccatggaag gccaaccatg agacacatcg ccaacctggg tgtcatttct | 2580 |
| cagaactag | 2589 |

<210> SEQ ID NO 4
<211> LENGTH: 2340
<212> TYPE: DNA
<213> ORGANISM: Arabidopsis thaliana

<400> SEQUENCE: 4

| | |
|---|---|
| atgcaaggag attcttctcc gtctccgacg actactagct ctccttttgat aagacctata | 60 |
| aacagaaacg taattcacag aatctgttcc ggtcaagtca tcttagacct ctcttcggcc | 120 |
| gtcaaggagc ttgtcgagaa tagtctcgac gccggcgcca ccagtataga gattaacctc | 180 |
| cgagactacg gcgaagacta ttttcaggtc attgacaatg ttgtggcat ttccccaacc | 240 |
| aatttcaagg tttgtgtcca aattctccga agaacttttg atgttcttgc acttaagcat | 300 |
| catacttcta aattagagga tttcacagat cttttgaatt tgactactta tggttttaga | 360 |
| ggagaagcct tgagctctct ctgtgcattg ggaaatctca ctgtggaaac aagaacaaag | 420 |
| aatgagccag ttgctacgct cttgacgttt gatcattctg gtttgcttac tgctgaaaag | 480 |
| aagactgctc gccaaattgg taccactgtc actgttagga agttgttctc taatttacct | 540 |
| gtacgaagca aagagtttaa gcggaatata cgcaaagaat atgggaagct tgtatcttta | 600 |
| ttgaacgcat atgcgcttat tgcgaaagga gtgcggtttg tctgctctaa cacgactggg | 660 |
| aaaaacccaa agtctgttgt gctgaacaca caagggaggg gttcacttaa agataatatc | 720 |
| ataacagttt tcggcattag taccttaca agtctacagc ctggtactgg acgcaattta | 780 |
| gcagatcgac agtatttctt tataaatggt cggcctgtag atatgccaaa agtcagcaag | 840 |
| ttggtgaatg agttatataa agatacaagt tctcggaaat atccagttac cattctggat | 900 |
| tttattgtgc ctggtggagc atgtgatttg aatgtcacgc ccgataaaag aaaggtgttc | 960 |

```
ttttctgacg agacttctgt tatcggttct ttgagggaag gtctgaacga gatatattcc   1020
tccagtaatg cgtcttatat tgttaatagg ttcgaggaga attcggagca accagataag   1080
gctggagttt cgtcgtttca gaagaaatca aatcttttgt cagaagggat agttctggat   1140
gtcagttcta aaacaagact aggggaagct attgagaaag aaaatccatc cttaagggag   1200
gttgaaattg ataatagttc gccaatggag aagtttaagt ttgagatcaa ggcatgtggg   1260
acgaagaaag gggaaggttc tttatcagtc catgatgtaa ctcaccttga caagacacct   1320
agcaaaggtt tgcctcagtt aaatgtgact gagaaagtta ctgatgcaag taaagacttg   1380
agcagccgct ctagctttgc ccagtcaact ttgaatactt ttgttaccat gggaaaaaga   1440
aaacatgaaa acataagcac catcctctct gaaacacctg tcctcagaaa ccaaacttct   1500
agttatcgtg tggagaaaag caaatttgaa gttcgtgcct tagcttcaag gtgtctcgtg   1560
gaaggcgatc aacttgatga tatggtcatc tcaaggaag atatgacacc aagcgaaaga   1620
gattctgaac taggcaatcg gatttctcct ggaacacaag ctgataatgt tgaaagacat   1680
gagagagtac tcgggcaatt caatcttggg ttcatcattg caaaattgga gcgagatctg   1740
ttcattgtgg atcagcatgc agctgatgag aaattcaact tcgaacattt agcaaggtca   1800
actgtcctga accagcaacc cttactccag cctttgaact tggaactctc tccagaagaa   1860
gaagtaactg tgttaatgca catggatatt atcagggaaa atggctttct tctagaggag   1920
aatccaagtg ctcctcccgg aaaacacttt agactacgag ccattcctta tagcaagaat   1980
atcacctttg gagtcgaaga tcttaaagac ctgatctcaa ctctaggaga taaccatggg   2040
gaatgttcgg ttgctagtag ctacaaaacc agcaaaacag attcgatttg tccatcacga   2100
gtccgtgcaa tgctagcatc ccgagcatgc agatcatctg tgatgatcgg agatccactc   2160
agaaaaaacg aaatgcagaa gatagtagaa cacttggcag atctcgaatc tccttggaat   2220
tgcccacacg gacgaccaac aatgcgtcat cttgtggact tgacaacttt actcacatta   2280
cctgatgacg acaatgtcaa tgatgatgat gatgatgatg caaccatctc attggcatga   2340
```

<210> SEQ ID NO 5
<211> LENGTH: 402
<212> TYPE: DNA
<213> ORGANISM: Human sapiens

<400> SEQUENCE: 5

```
atggagcgag ctgagagctc gagtacagaa cctgctaagg ccatcaaacc tattgatcgg    60
aagtcagtcc atcagatttg ctctgggcag gtggtactga gtctaagcac tgcggtaaag   120
gagttagtag aaaacagtct ggatgctggt gccactaata ttgatctaaa gcttaaggac   180
tatggagtgg atcttattga agtttcagac aatggatgtg gggtagaaga agaaaacttc   240
gaaggcttaa ctctgaaaca tcacacatct aagattcaag agtttgccga cctaactcag   300
gttgaaactt ttggctttcg gggggaagct ctgagctcac tttgtgcact gagcgatgtc   360
accatttcta cctgccacgc atcggcgaag gttggaactt ag                      402
```

<210> SEQ ID NO 6
<211> LENGTH: 441
<212> TYPE: DNA
<213> ORGANISM: Arabidopsis thaliana

<400> SEQUENCE: 6

```
atgcaaggag attcttctcc gtctccgacg actactagct ctcctttgat aagacctata    60
aacagaaacg taattcacag aatctgttcc ggtcaagtca tcttagacct ctcttcggcc   120
```

-continued

```
gtcaaggagc ttgtcgagaa tagtctcgac gccggcgcca ccagtataga gattaacctc    180
cgagactacg gcgaagacta ttttcaggtc attgacaatg gttgtggcat ttccccaacc    240
aatttcaagg tttgtgtcca aattctccga agaactttttg atgttcttgc acttaagcat    300
catacttcta aattagagga tttcacagat cttttgaatt tgactactta tggttttaga    360
ggagaagcct tgagctctct ctgtgcattg ggaaatctca ctgtggaaac aagaacaaag    420
aatgagccag ttgctacgct c                                               441
```

<210> SEQ ID NO 7
<211> LENGTH: 27
<212> TYPE: DNA
<213> ORGANISM: Human sapiens

<400> SEQUENCE: 7

```
tctagacatg gagcgagctg agagctc                                         27
```

<210> SEQ ID NO 8
<211> LENGTH: 27
<212> TYPE: DNA
<213> ORGANISM: Human sapiens

<400> SEQUENCE: 8

```
tctagaagtt ccaaccttcg ccgatgc                                         27
```

<210> SEQ ID NO 9
<211> LENGTH: 737
<212> TYPE: PRT
<213> ORGANISM: Arabidopsis thaliana

<400> SEQUENCE: 9

Met Ile Asp Asp Ser Ser Leu Thr Ala Glu Met Glu Glu Glu Glu Ser
1               5                   10                  15

Pro Ala Thr Thr Ile Val Pro Arg Glu Pro Pro Lys Ile Gln Arg Leu
            20                  25                  30

Glu Glu Ser Val Val Asn Arg Ile Ala Ala Gly Glu Val Ile Gln Arg
        35                  40                  45

Pro Val Ser Ala Val Lys Glu Leu Val Glu Asn Ser Leu Asp Ala Asp
    50                  55                  60

Ser Ser Ser Ile Ser Val Val Lys Asp Gly Gly Leu Lys Leu Ile
65                  70                  75                  80

Gln Val Ser Asp Asp Gly His Gly Ile Arg Arg Glu Asp Leu Pro Ile
                85                  90                  95

Leu Cys Glu Arg His Thr Thr Ser Lys Leu Thr Lys Phe Glu Asp Leu
            100                 105                 110

Phe Ser Leu Ser Ser Met Gly Phe Arg Gly Glu Ala Leu Ala Ser Met
        115                 120                 125

Thr Tyr Val Ala His Val Thr Val Thr Thr Ile Thr Lys Gly Gln Ile
    130                 135                 140

His Gly Tyr Arg Val Ser Tyr Arg Asp Gly Val Met Glu His Glu Pro
145                 150                 155                 160

Lys Ala Cys Ala Ala Val Lys Gly Thr Gln Ile Met Val Glu Asn Leu
                165                 170                 175

Phe Tyr Asn Met Ile Ala Arg Arg Lys Thr Leu Gln Asn Ser Ala Asp
            180                 185                 190

Asp Tyr Gly Lys Ile Val Asp Leu Leu Ser Arg Met Ala Ile His Tyr
        195                 200                 205

-continued

Asn Asn Val Ser Phe Ser Cys Arg Lys His Gly Ala Val Lys Ala Asp
    210                 215                 220

Val His Ser Val Val Ser Pro Ser Arg Leu Asp Ser Ile Arg Ser Val
225                 230                 235                 240

Tyr Gly Val Ser Val Ala Lys Asn Leu Met Lys Val Glu Val Ser Ser
                245                 250                 255

Cys Asp Ser Ser Gly Cys Thr Phe Asp Met Glu Gly Phe Ile Ser Asn
            260                 265                 270

Ser Asn Tyr Val Ala Lys Lys Thr Ile Leu Val Leu Phe Ile Asn Asp
        275                 280                 285

Arg Leu Val Glu Cys Ser Ala Leu Lys Arg Ala Ile Glu Ile Val Tyr
    290                 295                 300

Ala Ala Thr Leu Pro Lys Ala Ser Lys Pro Phe Val Tyr Met Ser Ile
305                 310                 315                 320

Asn Leu Pro Arg Glu His Val Asp Ile Asn Ile His Pro Thr Lys Lys
                325                 330                 335

Glu Val Ser Leu Leu Asn Gln Glu Ile Ile Glu Met Ile Gln Ser
            340                 345                 350

Glu Val Glu Val Lys Leu Arg Asn Ala Asn Asp Thr Arg Thr Phe Gln
        355                 360                 365

Glu Gln Lys Val Glu Tyr Ile Gln Ser Thr Leu Thr Ser Gln Lys Ser
    370                 375                 380

Asp Ser Pro Val Ser Gln Lys Pro Ser Gly Gln Lys Thr Gln Lys Val
385                 390                 395                 400

Pro Val Asn Lys Met Val Arg Thr Asp Ser Ser Asp Pro Ala Gly Arg
                405                 410                 415

Leu His Ala Phe Leu Gln Pro Lys Pro Gln Ser Leu Pro Asp Lys Val
            420                 425                 430

Ser Ser Leu Ser Val Val Arg Ser Val Arg Gln Arg Arg Asn Pro
        435                 440                 445

Lys Glu Thr Ala Asp Leu Ser Ser Val Gln Glu Leu Ile Ala Gly Val
    450                 455                 460

Asp Ser Cys Cys His Pro Gly Met Leu Glu Thr Val Arg Asn Cys Thr
465                 470                 475                 480

Tyr Val Gly Met Ala Asp Asp Val Phe Ala Leu Val Gln Tyr Asn Thr
                485                 490                 495

His Leu Tyr Leu Ala Asn Val Val Asn Leu Ser Lys Glu Leu Met Tyr
            500                 505                 510

Gln Gln Thr Leu Arg Arg Phe Ala His Phe Asn Ala Ile Gln Leu Ser
        515                 520                 525

Asp Pro Ala Pro Leu Ser Glu Leu Ile Leu Leu Ala Leu Lys Glu Glu
    530                 535                 540

Asp Leu Asp Pro Gly Asn Asp Thr Lys Asp Leu Lys Glu Arg Ile
545                 550                 555                 560

Ala Glu Met Asn Thr Glu Leu Leu Lys Glu Lys Ala Glu Met Leu Glu
                565                 570                 575

Glu Tyr Phe Ser Val His Ile Asp Ser Ser Ala Asn Leu Ser Arg Leu
            580                 585                 590

Pro Val Ile Leu Asp Gln Tyr Thr Pro Asp Met Asp Arg Val Pro Glu
        595                 600                 605

Phe Leu Leu Cys Leu Gly Asn Asp Val Glu Trp Glu Asp Glu Lys Ser
    610                 615                 620

Cys Phe Gln Gly Val Ser Ala Ala Ile Gly Asn Phe Tyr Ala Met His
625                 630                 635                 640

-continued

```
Pro Pro Leu Leu Pro Asn Pro Ser Gly Asp Gly Ile Gln Phe Tyr Ser
            645                 650                 655

Lys Arg Gly Glu Ser Ser Gln Glu Lys Ser Asp Leu Glu Gly Asn Val
        660                 665                 670

Asp Met Glu Asp Asn Leu Asp Gln Asp Leu Leu Ser Asp Ala Glu Asn
    675                 680                 685

Ala Trp Ala Gln Arg Glu Trp Ser Ile Gln His Val Leu Phe Pro Ser
690                 695                 700

Met Arg Leu Phe Leu Lys Pro Pro Ala Ser Met Ala Ser Asn Gly Thr
705                 710                 715                 720

Phe Val Lys Val Ala Ser Leu Glu Lys Leu Tyr Lys Ile Phe Glu Arg
                725                 730                 735

Cys

<210> SEQ ID NO 10
<211> LENGTH: 1151
<212> TYPE: PRT
<213> ORGANISM: Arabidopsis thaliana

<400> SEQUENCE: 10

Met Lys Thr Ile Lys Pro Leu Pro Glu Gly Val Arg His Ser Met Arg
1               5                   10                  15

Ser Gly Ile Ile Met Phe Asp Met Ala Arg Val Val Glu Glu Leu Val
            20                  25                  30

Phe Asn Ser Leu Asp Ala Gly Ala Thr Lys Val Ser Ile Phe Val Gly
        35                  40                  45

Val Val Ser Cys Ser Val Lys Val Val Asp Asp Gly Ser Gly Val Ser
    50                  55                  60

Arg Asp Asp Leu Val Leu Leu Gly Glu Arg Tyr Ala Thr Ser Lys Phe
65                  70                  75                  80

His Asp Phe Thr Asn Val Glu Thr Ala Ser Glu Thr Phe Gly Phe Arg
                85                  90                  95

Gly Glu Ala Leu Ala Ser Ile Ser Asp Ile Ser Leu Leu Glu Val Arg
            100                 105                 110

Thr Lys Ala Ile Gly Arg Pro Asn Gly Tyr Arg Lys Val Met Lys Gly
        115                 120                 125

Ser Lys Cys Leu His Leu Gly Ile Asp Asp Arg Lys Asp Ser Gly
    130                 135                 140

Thr Thr Val Thr Val Arg Asp Leu Phe Tyr Ser Gln Pro Val Arg Arg
145                 150                 155                 160

Lys Tyr Met Gln Ser Ser Pro Lys Lys Val Leu Glu Ser Ile Lys Lys
                165                 170                 175

Cys Val Phe Arg Ile Ala Leu Val His Ser Asn Val Ser Phe Ser Val
            180                 185                 190

Leu Asp Ile Glu Ser Asp Glu Glu Leu Phe Gln Thr Asn Pro Ser Ser
        195                 200                 205

Ser Ala Phe Ser Leu Leu Met Arg Asp Ala Gly Thr Glu Ala Val Asn
    210                 215                 220

Ser Leu Cys Lys Val Asn Val Thr Asp Gly Met Leu Asn Val Ser Gly
225                 230                 235                 240

Phe Glu Cys Ala Asp Asp Trp Lys Pro Thr Asp Gly Gln Gln Thr Gly
                245                 250                 255

Arg Arg Asn Arg Leu Gln Ser Asn Pro Gly Tyr Ile Leu Cys Ile Ala
            260                 265                 270
```

```
Cys Pro Arg Arg Leu Tyr Glu Phe Ser Phe Glu Pro Ser Lys Thr His
    275                 280                 285
Val Glu Phe Lys Lys Trp Gly Pro Val Leu Ala Phe Ile Glu Arg Ile
    290                 295                 300
Thr Leu Ala Asn Trp Lys Lys Asp Arg Ile Leu Glu Leu Phe Asp Gly
305                 310                 315                 320
Gly Ala Asp Ile Leu Ala Lys Gly Asp Arg Gln Asp Leu Ile Asp Asp
                325                 330                 335
Lys Ile Arg Leu Gln Asn Gly Ser Leu Phe Ser Ile Leu His Phe Leu
                340                 345                 350
Asp Ala Asp Trp Pro Glu Ala Met Glu Pro Ala Lys Lys Lys Leu Lys
                355                 360                 365
Arg Ser Asn Asp His Ala Pro Cys Ser Ser Leu Leu Phe Pro Ser Ala
    370                 375                 380
Asp Phe Lys Gln Asp Gly Asp Tyr Phe Ser Pro Arg Lys Asp Val Trp
385                 390                 395                 400
Ser Pro Glu Cys Glu Val Glu Leu Lys Ile Gln Asn Pro Lys Glu Gln
                405                 410                 415
Gly Thr Val Ala Gly Phe Glu Ser Arg Thr Asp Ser Leu Leu Gln Ser
                420                 425                 430
Arg Asp Ile Glu Met Gln Thr Asn Glu Asp Phe Pro Gln Val Thr Asp
                435                 440                 445
Leu Leu Glu Thr Ser Leu Val Ala Asp Ser Lys Cys Arg Lys Gln Phe
450                 455                 460
Leu Thr Arg Cys Gln Ile Thr Thr Pro Val Asn Ile Asn His Asp Phe
465                 470                 475                 480
Met Lys Asp Ser Asp Val Leu Asn Phe Gln Phe Gln Gly Leu Lys Asp
                485                 490                 495
Glu Leu Asp Val Ser Asn Cys Ile Gly Lys His Leu Leu Arg Gly Cys
                500                 505                 510
Ser Ser Arg Val Ser Leu Thr Phe His Glu Pro Lys Leu Ser His Val
                515                 520                 525
Glu Gly Tyr Glu Ser Val Val Pro Met Ile Pro Asn Glu Lys Gln Ser
                530                 535                 540
Ser Pro Arg Val Leu Glu Thr Arg Glu Gly Gly Ser Tyr Cys Asp Val
545                 550                 555                 560
Tyr Ser Asp Lys Thr Pro Asp Cys Ser Leu Gly Ser Ser Trp Gln Asp
                565                 570                 575
Thr Asp Trp Phe Thr Pro Gln Cys Ser Ser Asp Arg Gly Cys Val Gly
                580                 585                 590
Ile Gly Glu Asp Phe Asn Ile Thr Pro Ile Asp Thr Ala Glu Phe Asp
                595                 600                 605
Ser Tyr Asp Glu Lys Val Gly Ser Lys Lys Tyr Leu Ser Ser Val Asn
                610                 615                 620
Val Gly Ser Ser Val Thr Gly Ser Phe Cys Leu Ser Ser Glu Trp Ser
625                 630                 635                 640
Pro Met Tyr Ser Thr Pro Ser Ala Thr Lys Trp Glu Ser Glu Tyr Gln
                645                 650                 655
Lys Gly Cys Arg Ile Leu Glu Gln Ser Leu Arg Leu Gly Arg Met Pro
                660                 665                 670
Asp Pro Glu Phe Cys Phe Ser Ala Ala Asn Asn Ile Lys Phe Asp His
                675                 680                 685
Glu Val Ile Pro Glu Met Asp Cys Cys Glu Thr Gly Thr Asp Ser Phe
                690                 695                 700
```

-continued

```
Thr Ala Ile Gln Asn Cys Thr Gln Leu Ala Asp Lys Ile Cys Lys Ser
705                 710                 715                 720

Ser Trp Gly His Ala Asp Asp Val Arg Ile Asp Gln Tyr Ser Ile Arg
            725                 730                 735

Lys Glu Lys Phe Ser Tyr Met Asp Gly Thr Gln Asn Asn Ala Gly Lys
        740                 745                 750

Gln Arg Ser Lys Arg Ser Arg Ser Ala Pro Pro Phe Tyr Arg Glu Lys
    755                 760                 765

Lys Arg Phe Ile Ser Leu Ser Cys Lys Ser Asp Thr Lys Pro Lys Asn
770                 775                 780

Ser Asp Pro Ser Glu Pro Asp Leu Glu Cys Leu Thr Gln Pro Cys
785                 790                 795                 800

Asn Ala Ser Gln Met His Leu Lys Cys Ser Ile Leu Asp Asp Val Ser
                805                 810                 815

Tyr Asp His Ile Gln Glu Thr Glu Lys Arg Leu Ser Ser Ala Ser Asp
            820                 825                 830

Leu Lys Ala Ser Ala Gly Cys Arg Thr Val His Ser Glu Thr Gln Asp
        835                 840                 845

Glu Asp Val His Glu Asp Phe Ser Ser Glu Gly Phe Leu Asp Pro Ile
850                 855                 860

Lys Ser Thr Thr Lys Trp Arg His Asn Cys Ala Val Ser Gln Val Pro
865                 870                 875                 880

Lys Glu Ser His Glu Leu His Gly Gln Asp Gly Val Phe Asp Ile Ser
                885                 890                 895

Ser Gly Leu Leu His Leu Arg Ser Asp Glu Ser Leu Val Pro Glu Ser
            900                 905                 910

Ile Asn Arg His Ser Leu Glu Asp Ala Lys Val Leu Gln Gln Val Asp
        915                 920                 925

Lys Lys Tyr Ile Pro Ile Val Ala Cys Gly Thr Val Ala Ile Val Asp
930                 935                 940

Gln His Ala Ala Asp Glu Arg Ile Arg Leu Glu Glu Leu Arg Thr Lys
945                 950                 955                 960

Phe Ile Asn Asp Ala Leu Leu Ile Phe Val Leu Thr Leu Lys Val Leu
                965                 970                 975

Pro Glu Met Gly Tyr Gln Leu Leu Gln Ser Tyr Ser Glu Gln Ile Arg
            980                 985                 990

Asp Trp Gly Trp Ile Cys Asn Ile Thr Val Glu Gly Ser Thr Ser Phe
        995                 1000                1005

Lys Lys Asn Met Ser Ile Ile Gln Arg Lys Pro Thr Pro Ile Thr Leu
1010                1015                1020

Asn Ala Val Pro Cys Ile Leu Gly Val Asn Leu Ser Asp Val Asp Leu
1025                1030                1035                1040

Leu Glu Phe Leu Gln Gln Leu Ala Asp Thr Asp Gly Ser Ser Thr Ile
                1045                1050                1055

Pro Pro Ser Val Leu Arg Val Leu Asn Ser Lys Ala Cys Arg Gly Ala
            1060                1065                1070

Ile Met Phe Gly Asp Ser Leu Leu Pro Ser Glu Cys Ser Leu Ile Ile
        1075                1080                1085

Asp Gly Leu Lys Gln Thr Ser Leu Cys Phe Gln Cys Ala His Gly Arg
1090                1095                1100

Pro Thr Thr Val Pro Leu Val Asp Leu Lys Ala Leu His Lys Gln Ile
1105                1110                1115                1120
```

```
Ala Lys Leu Ser Gly Arg Gln Val Trp His Gly Leu Gln Arg Arg Glu
            1125                1130                1135

Ile Thr Leu Asp Arg Ala Lys Ser Arg Leu Asp Asn Ala Lys Ser
            1140                1145                1150

<210> SEQ ID NO 11
<211> LENGTH: 862
<212> TYPE: PRT
<213> ORGANISM: Homo sapiens

<400> SEQUENCE: 11

Met Glu Arg Ala Glu Ser Ser Ser Thr Glu Pro Ala Lys Ala Ile Lys
  1               5                  10                  15

Pro Ile Asp Arg Lys Ser Val His Gln Ile Cys Ser Gly Gln Val Val
             20                  25                  30

Leu Ser Leu Ser Thr Ala Val Lys Glu Leu Val Glu Asn Ser Leu Asp
         35                  40                  45

Ala Gly Ala Thr Asn Ile Asp Leu Lys Leu Lys Asp Tyr Gly Val Asp
     50                  55                  60

Leu Ile Glu Val Ser Asp Asn Gly Cys Gly Val Glu Glu Asn Phe
 65                  70                  75                  80

Glu Gly Leu Thr Leu Lys His His Thr Ser Lys Ile Gln Glu Phe Ala
                 85                  90                  95

Asp Leu Thr Gln Val Glu Thr Phe Gly Phe Arg Gly Glu Ala Leu Ser
            100                 105                 110

Ser Leu Cys Ala Leu Ser Asp Val Thr Ile Ser Thr Cys His Ala Ser
        115                 120                 125

Ala Lys Val Gly Thr Arg Leu Met Phe Asp His Asn Gly Lys Ile Ile
    130                 135                 140

Gln Lys Thr Pro Tyr Pro Arg Pro Arg Gly Thr Thr Val Ser Val Gln
145                 150                 155                 160

Gln Leu Phe Ser Thr Leu Pro Val Arg His Lys Glu Phe Gln Arg Asn
                165                 170                 175

Ile Lys Lys Glu Tyr Ala Lys Met Val Gln Val Leu His Ala Tyr Cys
            180                 185                 190

Ile Ile Ser Ala Gly Ile Arg Val Ser Cys Thr Asn Gln Leu Gly Gln
        195                 200                 205

Gly Lys Arg Gln Pro Val Val Cys Thr Gly Gly Ser Pro Ser Ile Lys
    210                 215                 220

Glu Asn Ile Gly Ser Val Phe Gly Gln Lys Gln Leu Gln Ser Leu Ile
225                 230                 235                 240

Pro Phe Val Gln Leu Pro Pro Ser Asp Ser Val Cys Glu Glu Tyr Gly
                245                 250                 255

Leu Ser Cys Ser Asp Ala Leu His Asn Leu Phe Tyr Ile Ser Gly Phe
            260                 265                 270

Ile Ser Gln Cys Thr His Gly Val Gly Arg Ser Ser Thr Asp Arg Gln
        275                 280                 285

Phe Phe Phe Ile Asn Arg Arg Pro Cys Asp Pro Ala Lys Val Cys Arg
    290                 295                 300

Leu Val Asn Glu Val Tyr His Met Tyr Asn Arg His Gln Tyr Pro Phe
305                 310                 315                 320

Val Val Leu Asn Ile Ser Val Asp Ser Glu Cys Val Asp Ile Asn Val
                325                 330                 335

Thr Pro Asp Lys Arg Gln Ile Leu Leu Gln Glu Glu Lys Leu Leu Leu
            340                 345                 350
```

```
Ala Val Leu Lys Thr Ser Leu Ile Gly Met Phe Asp Ser Asp Val Asn
            355                 360                 365

Lys Leu Asn Val Ser Gln Gln Pro Leu Leu Asp Val Glu Gly Asn Leu
370                 375                 380

Ile Lys Met His Ala Ala Asp Leu Glu Lys Pro Met Val Glu Lys Gln
385                 390                 395                 400

Asp Gln Ser Pro Ser Leu Arg Thr Gly Glu Glu Lys Lys Asp Val Ser
            405                 410                 415

Ile Ser Arg Leu Arg Glu Ala Phe Ser Leu Arg His Thr Thr Glu Asn
                420                 425                 430

Lys Pro His Ser Pro Lys Thr Pro Glu Pro Arg Ser Pro Leu Gly
            435                 440                 445

Gln Lys Arg Gly Met Leu Ser Ser Ser Thr Ser Gly Ala Ile Ser Asp
450                 455                 460

Lys Gly Val Leu Arg Pro Gln Lys Glu Ala Val Ser Ser Ser His Gly
465                 470                 475                 480

Pro Ser Asp Pro Thr Asp Arg Ala Glu Val Glu Lys Asp Ser Gly His
                485                 490                 495

Gly Ser Thr Ser Val Asp Ser Glu Gly Phe Ser Ile Pro Asp Thr Gly
            500                 505                 510

Ser His Cys Ser Ser Glu Tyr Ala Ala Ser Ser Pro Gly Asp Arg Gly
            515                 520                 525

Ser Gln Glu His Val Asp Ser Gln Glu Lys Ala Pro Glu Thr Asp Asp
530                 535                 540

Ser Phe Ser Asp Val Asp Cys His Ser Asn Gln Glu Asp Thr Gly Cys
545                 550                 555                 560

Lys Phe Arg Val Leu Pro Gln Pro Thr Asn Leu Ala Thr Pro Asn Thr
                565                 570                 575

Lys Arg Phe Lys Lys Glu Glu Ile Leu Ser Ser Ser Asp Ile Cys Gln
            580                 585                 590

Lys Leu Val Asn Thr Gln Asp Met Ser Ala Ser Gln Val Asp Val Ala
            595                 600                 605

Val Lys Ile Asn Lys Lys Val Val Pro Leu Asp Phe Ser Met Ser Ser
610                 615                 620

Leu Ala Lys Arg Ile Lys Gln Leu His His Glu Ala Gln Gln Ser Glu
625                 630                 635                 640

Gly Glu Gln Asn Tyr Arg Lys Phe Arg Ala Lys Ile Cys Pro Gly Glu
                645                 650                 655

Asn Gln Ala Ala Glu Asp Glu Leu Arg Lys Glu Ile Ser Lys Thr Met
            660                 665                 670

Phe Ala Glu Met Glu Ile Ile Gly Gln Phe Asn Leu Gly Phe Ile Ile
            675                 680                 685

Thr Lys Leu Asn Glu Asp Ile Phe Ile Val Asp Gln His Ala Thr Asp
690                 695                 700

Glu Lys Tyr Asn Phe Glu Met Leu Gln Gln His Thr Val Leu Gln Gly
705                 710                 715                 720

Gln Arg Leu Ile Ala Pro Gln Thr Leu Asn Leu Thr Ala Val Asn Glu
                725                 730                 735

Ala Val Leu Ile Glu Asn Leu Glu Ile Phe Arg Lys Asn Gly Phe Asp
            740                 745                 750

Phe Val Ile Asp Glu Asn Ala Pro Val Thr Glu Arg Ala Lys Leu Ile
            755                 760                 765

Ser Leu Pro Thr Ser Lys Asn Trp Thr Phe Gly Pro Gln Asp Val Asp
770                 775                 780
```

Glu Leu Ile Phe Met Leu Ser Asp Ser Pro Gly Val Met Cys Arg Pro
785                 790                 795                 800

Ser Arg Val Lys Gln Met Phe Ala Ser Arg Ala Cys Arg Lys Ser Val
            805                 810                 815

Met Ile Gly Thr Ala Leu Asn Thr Ser Glu Met Lys Lys Leu Ile Thr
            820                 825                 830

His Met Gly Glu Met Asp His Pro Trp Asn Cys Pro His Gly Arg Pro
            835                 840                 845

Thr Met Arg His Ile Ala Asn Leu Gly Val Ile Ser Gln Asn
            850                 855                 860

<210> SEQ ID NO 12
<211> LENGTH: 779
<212> TYPE: PRT
<213> ORGANISM: Arabidopsis thaliana

<400> SEQUENCE: 12

Met Gln Gly Asp Ser Ser Pro Ser Pro Thr Thr Thr Ser Ser Pro Leu
1               5                   10                  15

Ile Arg Pro Ile Asn Arg Asn Val Ile His Arg Ile Cys Ser Gly Gln
            20                  25                  30

Val Ile Leu Asp Leu Ser Ser Ala Val Lys Glu Leu Val Glu Asn Ser
        35                  40                  45

Leu Asp Ala Gly Ala Thr Ser Ile Glu Ile Asn Leu Arg Asp Tyr Gly
50                  55                  60

Glu Asp Tyr Phe Gln Val Ile Asp Asn Gly Cys Gly Ile Ser Pro Thr
65                  70                  75                  80

Asn Phe Lys Val Cys Val Gln Ile Leu Arg Arg Thr Phe Asp Val Leu
                85                  90                  95

Ala Leu Lys His His Thr Ser Lys Leu Glu Asp Phe Thr Asp Leu Leu
            100                 105                 110

Asn Leu Thr Thr Tyr Gly Phe Arg Gly Glu Ala Leu Ser Ser Leu Cys
        115                 120                 125

Ala Leu Gly Asn Leu Thr Val Glu Thr Arg Thr Lys Asn Glu Pro Val
130                 135                 140

Ala Thr Leu Leu Thr Phe Asp His Ser Gly Leu Leu Thr Ala Glu Lys
145                 150                 155                 160

Lys Thr Ala Arg Gln Ile Gly Thr Thr Val Thr Val Arg Lys Leu Phe
                165                 170                 175

Ser Asn Leu Pro Val Arg Ser Lys Glu Phe Lys Arg Asn Ile Arg Lys
            180                 185                 190

Glu Tyr Gly Lys Leu Val Ser Leu Leu Asn Ala Tyr Ala Leu Ile Ala
        195                 200                 205

Lys Gly Val Arg Phe Val Cys Ser Asn Thr Thr Gly Lys Asn Pro Lys
210                 215                 220

Ser Val Val Leu Asn Thr Gln Gly Arg Gly Ser Leu Lys Asp Asn Ile
225                 230                 235                 240

Ile Thr Val Phe Gly Ile Ser Thr Phe Thr Ser Leu Gln Pro Gly Thr
                245                 250                 255

Gly Arg Asn Leu Ala Asp Arg Gln Tyr Phe Phe Ile Asn Gly Arg Pro
            260                 265                 270

Val Asp Met Pro Lys Val Ser Lys Leu Val Asn Glu Leu Tyr Lys Asp
        275                 280                 285

Thr Ser Ser Arg Lys Tyr Pro Val Thr Ile Leu Asp Phe Ile Val Pro
290                 295                 300

```
Gly Gly Ala Cys Asp Leu Asn Val Thr Pro Asp Lys Arg Lys Val Phe
305                 310                 315                 320

Phe Ser Asp Glu Thr Ser Val Ile Gly Ser Leu Arg Glu Gly Leu Asn
                325                 330                 335

Glu Ile Tyr Ser Ser Ser Asn Ala Ser Tyr Ile Val Asn Arg Phe Glu
            340                 345                 350

Glu Asn Ser Glu Gln Pro Asp Lys Ala Gly Val Ser Ser Phe Gln Lys
        355                 360                 365

Lys Ser Asn Leu Leu Ser Glu Gly Ile Val Leu Asp Val Ser Ser Lys
370                 375                 380

Thr Arg Leu Gly Glu Ala Ile Glu Lys Glu Asn Pro Ser Leu Arg Glu
385                 390                 395                 400

Val Glu Ile Asp Asn Ser Ser Pro Met Glu Lys Phe Lys Phe Glu Ile
                405                 410                 415

Lys Ala Cys Gly Thr Lys Lys Gly Glu Gly Ser Leu Ser Val His Asp
            420                 425                 430

Val Thr His Leu Asp Lys Thr Pro Ser Lys Gly Leu Pro Gln Leu Asn
        435                 440                 445

Val Thr Glu Lys Val Thr Asp Ala Ser Lys Asp Leu Ser Ser Arg Ser
450                 455                 460

Ser Phe Ala Gln Ser Thr Leu Asn Thr Phe Val Thr Met Gly Lys Arg
465                 470                 475                 480

Lys His Glu Asn Ile Ser Thr Ile Leu Ser Glu Thr Pro Val Leu Arg
                485                 490                 495

Asn Gln Thr Ser Ser Tyr Arg Val Glu Lys Ser Lys Phe Glu Val Arg
            500                 505                 510

Ala Leu Ala Ser Arg Cys Leu Val Glu Gly Asp Gln Leu Asp Asp Met
        515                 520                 525

Val Ile Ser Lys Glu Asp Met Thr Pro Ser Glu Arg Asp Ser Glu Leu
530                 535                 540

Gly Asn Arg Ile Ser Pro Gly Thr Gln Ala Asp Asn Val Glu Arg His
545                 550                 555                 560

Glu Arg Val Leu Gly Gln Phe Asn Leu Gly Phe Ile Ile Ala Lys Leu
                565                 570                 575

Glu Arg Asp Leu Phe Ile Val Asp Gln His Ala Ala Asp Glu Lys Phe
            580                 585                 590

Asn Phe Glu His Leu Ala Arg Ser Thr Val Leu Asn Gln Gln Pro Leu
        595                 600                 605

Leu Gln Pro Leu Asn Leu Leu Ser Pro Glu Glu Val Thr Val
610                 615                 620

Leu Met His Met Asp Ile Ile Arg Glu Asn Gly Phe Leu Leu Glu Glu
625                 630                 635                 640

Asn Pro Ser Ala Pro Pro Gly Lys His Phe Arg Leu Arg Ala Ile Pro
                645                 650                 655

Tyr Ser Lys Asn Ile Thr Phe Gly Val Glu Asp Leu Lys Asp Leu Ile
            660                 665                 670

Ser Thr Leu Gly Asp Asn His Gly Glu Cys Ser Val Ala Ser Ser Tyr
        675                 680                 685

Lys Thr Ser Lys Thr Asp Ser Ile Cys Pro Ser Arg Val Arg Ala Met
690                 695                 700

Leu Ala Ser Arg Ala Cys Arg Ser Ser Val Met Ile Gly Asp Pro Leu
705                 710                 715                 720

Arg Lys Asn Glu Met Gln Lys Ile Val Glu His Leu Ala Asp Leu Glu
                725                 730                 735
```

```
Ser Pro Trp Asn Cys Pro His Gly Arg Pro Thr Met Arg His Leu Val
                740                 745                 750

Asp Leu Thr Thr Leu Leu Thr Leu Pro Asp Asp Asn Val Asn Asp
        755                 760                 765

Asp Asp Asp Asp Asp Ala Thr Ile Ser Leu Ala
        770                 775

<210> SEQ ID NO 13
<211> LENGTH: 133
<212> TYPE: PRT
<213> ORGANISM: Homo sapiens

<400> SEQUENCE: 13

Met Glu Arg Ala Glu Ser Ser Thr Glu Pro Ala Lys Ala Ile Lys
1               5                   10                  15

Pro Ile Asp Arg Lys Ser Val His Gln Ile Cys Ser Gly Gln Val
                20                  25                  30

Leu Ser Leu Ser Thr Ala Val Lys Glu Leu Val Glu Asn Ser Leu Asp
                35                  40                  45

Ala Gly Ala Thr Asn Ile Asp Leu Lys Leu Lys Asp Tyr Gly Val Asp
        50                  55                  60

Leu Ile Glu Val Ser Asp Asn Gly Cys Gly Val Glu Glu Asn Phe
65                  70                  75                  80

Glu Gly Leu Thr Leu Lys His His Thr Ser Lys Ile Gln Glu Phe Ala
                85                  90                  95

Asp Leu Thr Gln Val Glu Thr Phe Gly Phe Arg Gly Glu Ala Leu Ser
                100                 105                 110

Ser Leu Cys Ala Leu Ser Asp Val Thr Ile Ser Thr Cys His Ala Ser
            115                 120                 125

Ala Lys Val Gly Thr
        130

<210> SEQ ID NO 14
<211> LENGTH: 147
<212> TYPE: PRT
<213> ORGANISM: Arabidopsis thaliana

<400> SEQUENCE: 14

Met Gln Gly Asp Ser Ser Pro Ser Pro Thr Thr Thr Ser Ser Pro Leu
1               5                   10                  15

Ile Arg Pro Ile Asn Arg Asn Val Ile His Arg Ile Cys Ser Gly Gln
                20                  25                  30

Val Ile Leu Asp Leu Ser Ser Ala Val Lys Glu Leu Val Glu Asn Ser
            35                  40                  45

Leu Asp Ala Gly Ala Thr Ser Ile Glu Ile Asn Leu Arg Asp Tyr Gly
        50                  55                  60

Glu Asp Tyr Phe Gln Val Ile Asp Asn Gly Cys Gly Ile Ser Pro Thr
65                  70                  75                  80

Asn Phe Lys Val Cys Val Gln Ile Leu Arg Arg Thr Phe Asp Val Leu
                85                  90                  95

Ala Leu Lys His His Thr Ser Lys Leu Glu Asp Phe Thr Asp Leu Leu
                100                 105                 110

Asn Leu Thr Thr Tyr Gly Phe Arg Gly Glu Ala Leu Ser Ser Leu Cys
            115                 120                 125
```

-continued

```
Ala Leu Gly Asn Leu Thr Val Glu Thr Arg Thr Lys Asn Glu Pro Val
    130                 135                 140

Ala Thr Leu
145

<210> SEQ ID NO 15
<211> LENGTH: 54
<212> TYPE: DNA
<213> ORGANISM: Artificial Sequence
<220> FEATURE:
<223> OTHER INFORMATION: PCR primer

<400> SEQUENCE: 15
gtcgacttat cacttgtcat cgtcgtcctt gtagtcgagc gtagcaactg gctc      54
```